United States Patent
Lowery, Jr. et al.

(10) Patent No.: US 10,184,907 B2
(45) Date of Patent: Jan. 22, 2019

(54) MAGNETIC NANOSENSOR COMPOSITIONS AND BIOANALYTICAL ASSAYS THEREFOR

(71) Applicant: T2 Biosystems, Inc., Lexington, MA (US)

(72) Inventors: Thomas Jay Lowery, Jr., Belmont, MA (US); James Joseph Koziarz, Highland Park, IL (US); Douglas Adam Levinson, Sherborn, MA (US); David A. Berry, Brookline, MA (US); Tuan A. Elstrom, Lake Bluff, IL (US); Sonia Kumar, Brookline, MA (US); Mark John Audeh, Brighton, MA (US)

(73) Assignee: T2 Biosystems, Inc., Lexington, MA (US)

( * ) Notice: Subject to any disclaimer, the term of this patent is extended or adjusted under 35 U.S.C. 154(b) by 259 days.

(21) Appl. No.: 14/878,765

(22) Filed: Oct. 8, 2015

(65) Prior Publication Data

US 2016/0033494 A1 Feb. 4, 2016

Related U.S. Application Data

(62) Division of application No. 12/997,817, filed as application No. PCT/US2009/003946 on Jul. 2, 2009, now abandoned.

(Continued)

(51) Int. Cl.
*G01N 24/08* (2006.01)
*A61B 5/055* (2006.01)
(Continued)

(52) U.S. Cl.
CPC ............. *G01N 24/08* (2013.01); *A61B 5/055* (2013.01); *G01N 33/54326* (2013.01);
(Continued)

(58) Field of Classification Search
CPC ............... G01N 24/08; G01N 33/5436; G01N 33/54346; G01N 33/54353; Y10T 436/24; A61B 5/055

See application file for complete search history.

(56) References Cited

U.S. PATENT DOCUMENTS

| 4,452,773 A | * | 6/1984 | Molday | A61K 51/1251 |
| | | | | 210/632 |
| 4,795,698 A | * | 1/1989 | Owen | A61K 9/5094 |
| | | | | 252/62.56 |

(Continued)

OTHER PUBLICATIONS

International Search Report and Written Opinion for PCT/US09/03946, dated Sep. 21, 2009 (11 pages).

*Primary Examiner* — Jeremy C Flinders
(74) *Attorney, Agent, or Firm* — Clark & Elbing LLP

(57) ABSTRACT

Disclosed are magnetic nanosensors or transducers that permit measurement of a physical parameter in an analyte via magnetic reasonance measurements, in particular of non-agglomerative assays. More particularly, in certain embodiments, the invention relates to designs of nanoparticle reagents and responsive polymer coated magnetic nanoparticles. Additionally provided are methods of use of nanoparticle reagents and responsive polymer coated magnetic nanoparticles for the detection of a stimulus or an analyte with NMR detectors.

7 Claims, 12 Drawing Sheets

Related U.S. Application Data

(60) Provisional application No. 61/133,931, filed on Jul. 3, 2008.

(51) Int. Cl.

| | | |
|---|---|---|
| *G01N 33/543* | (2006.01) | |
| *A61B 5/145* | (2006.01) | |
| *A61B 5/1486* | (2006.01) | |
| *A61B 10/00* | (2006.01) | |
| *A61B 17/00* | (2006.01) | |

(52) U.S. Cl.
CPC .... *G01N 33/54346* (2013.01); *A61B 5/14532* (2013.01); *A61B 5/14865* (2013.01); *A61B 10/0045* (2013.01); *A61B 2017/00345* (2013.01); *Y10T 436/143333* (2015.01); *Y10T 436/144444* (2015.01); *Y10T 436/147777* (2015.01); *Y10T 436/16* (2015.01); *Y10T 436/171538* (2015.01); *Y10T 436/175383* (2015.01); *Y10T 436/19* (2015.01); *Y10T 436/201666* (2015.01); *Y10T 436/204998* (2015.01); *Y10T 436/207497* (2015.01); *Y10T 436/24* (2015.01)

(56) References Cited

U.S. PATENT DOCUMENTS

| | | | |
|---|---|---|---|
| 5,164,297 | A * | 11/1992 | Josephson ............ G01N 27/745 435/7.1 |
| 5,532,006 | A | 7/1996 | Lauterbur et al. |
| 6,546,268 | B1 | 4/2003 | Ishikawa et al. |
| 6,751,491 | B2 | 6/2004 | Lew et al. |
| 2003/0138490 | A1 | 7/2003 | Hu et al. |
| 2004/0158194 | A1 | 8/2004 | Wolff et al. |
| 2005/0287560 | A1 | 12/2005 | Garimella et al. |
| 2007/0116602 | A1 | 5/2007 | Lee |

\* cited by examiner

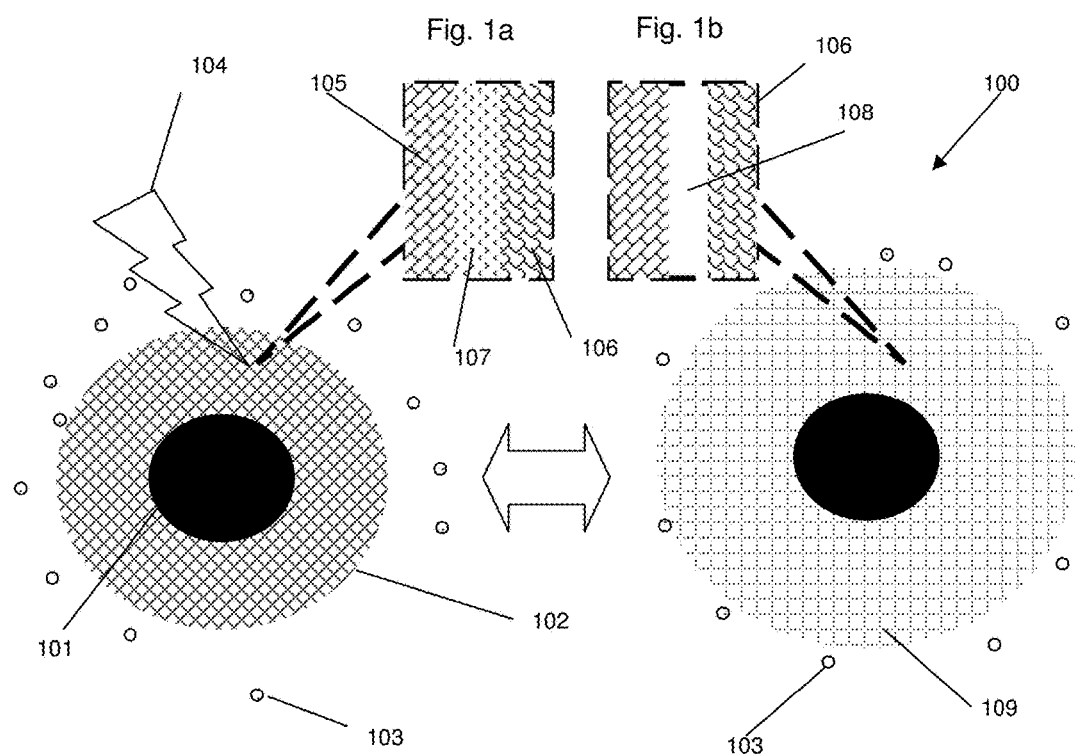

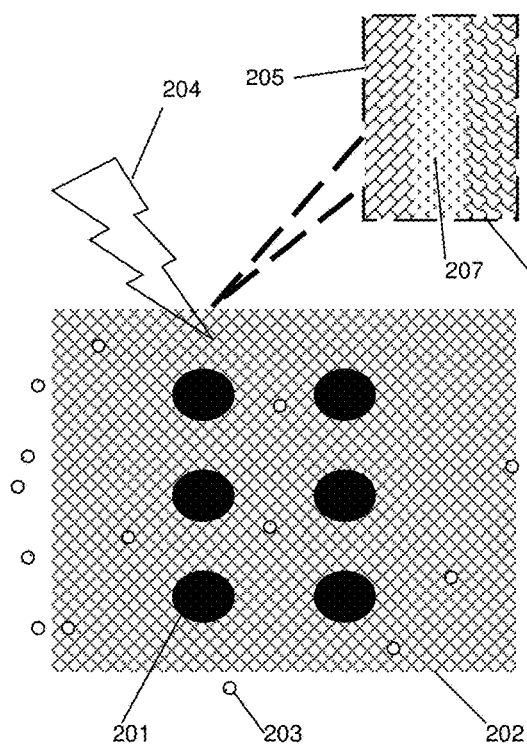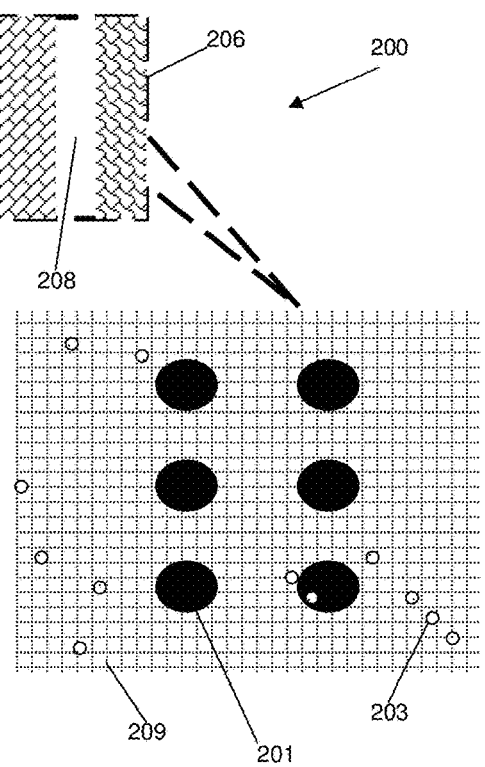

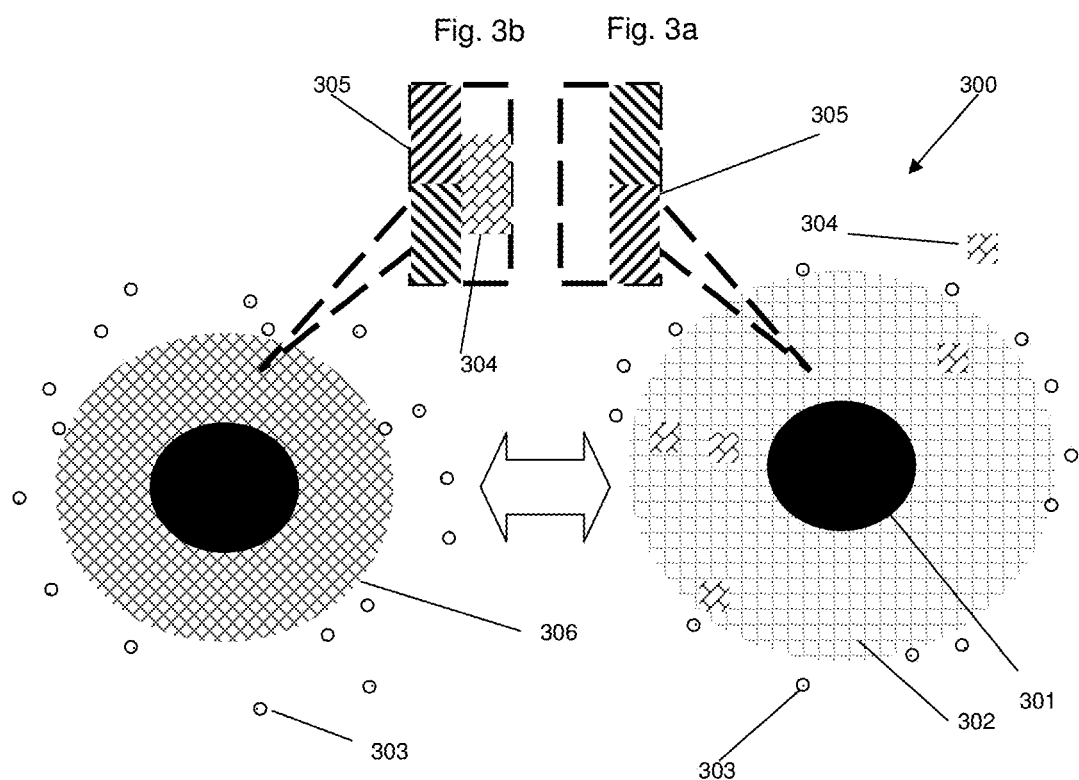

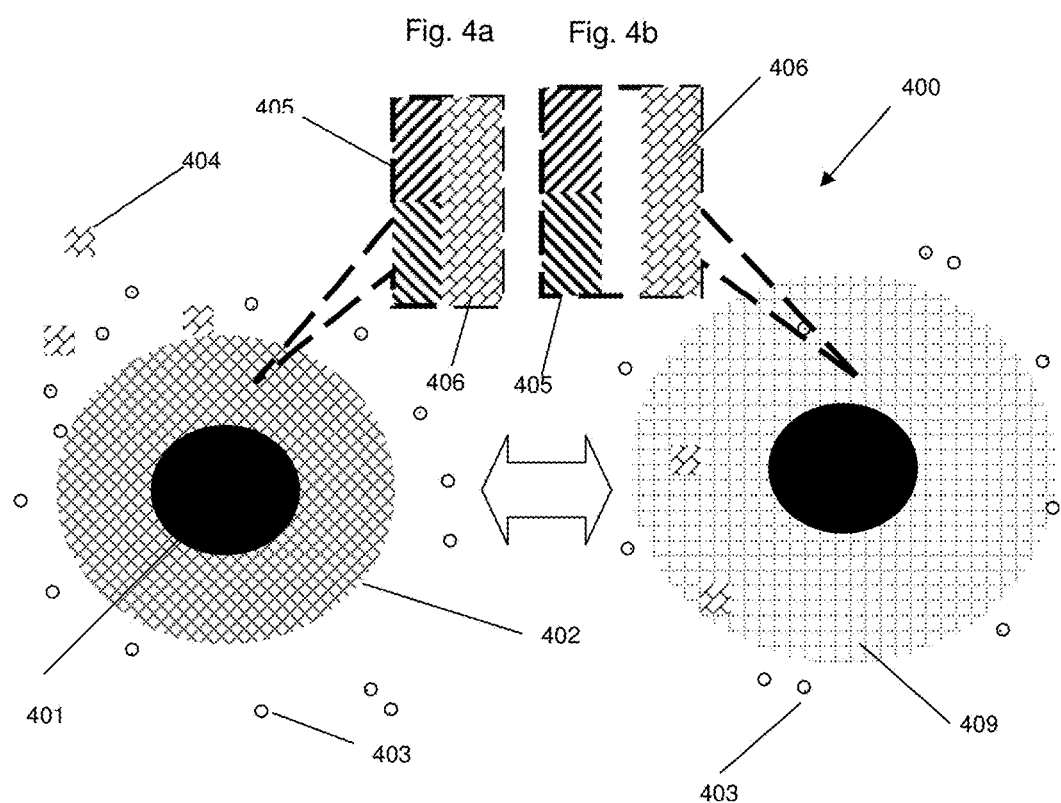

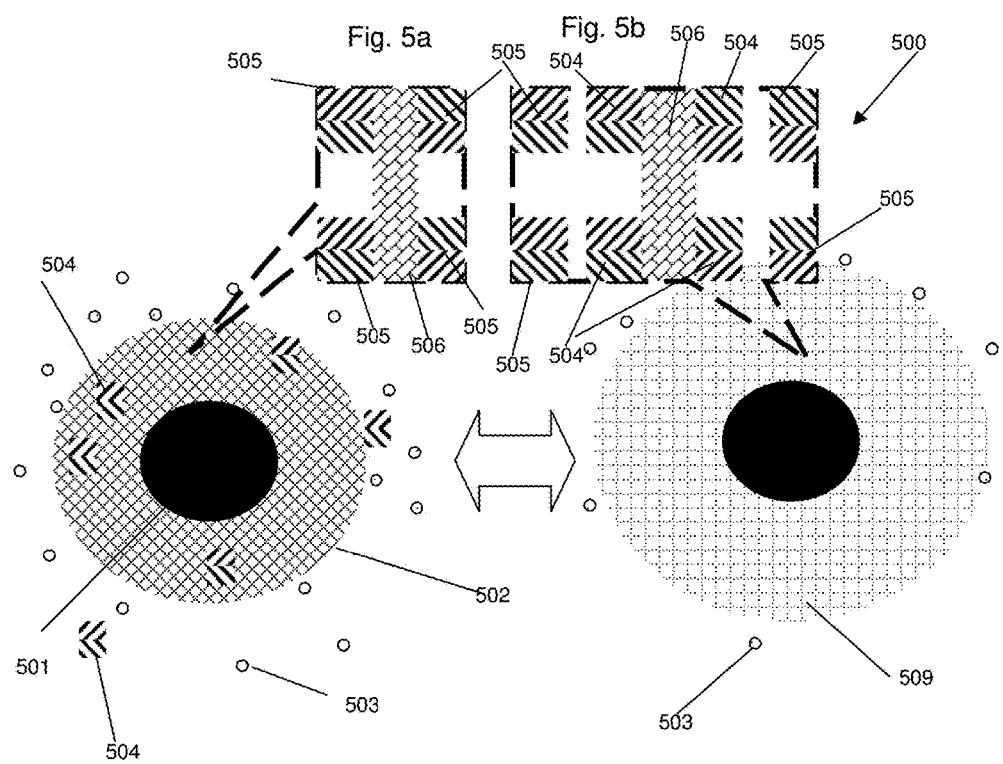

FIG 10
FIG 10A
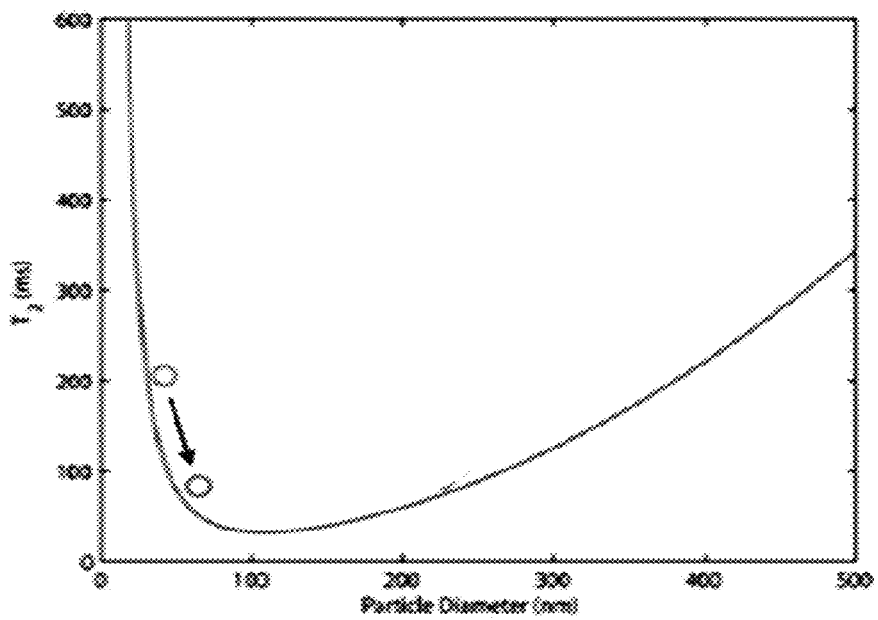
FIG 10B
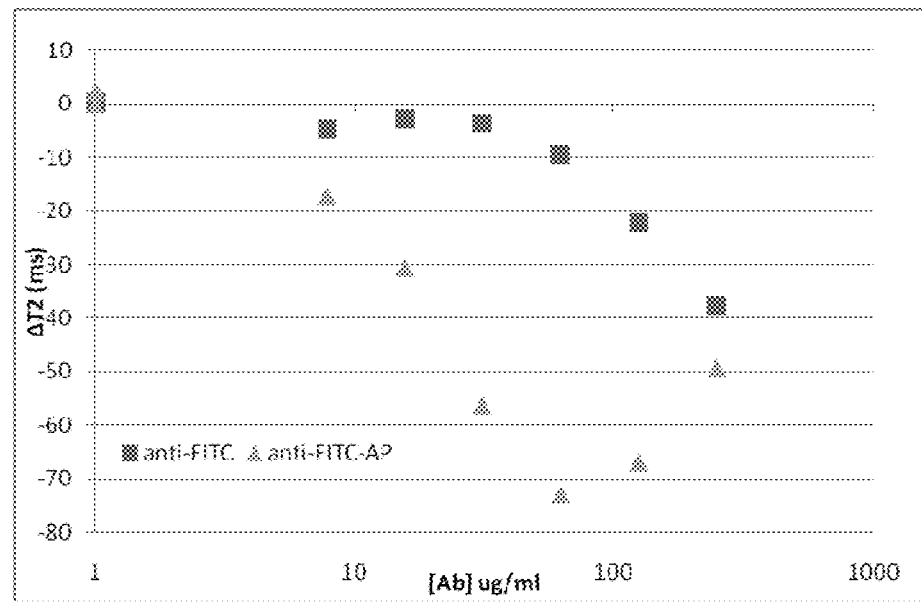

MAGNETIC NANOSENSOR COMPOSITIONS AND BIOANALYTICAL ASSAYS THEREFOR

FIELD OF THE INVENTION

This invention relates generally to NMR systems with magnetic nanosensors for detection of analytes. More particularly, in certain embodiments, the invention relates to NMR-based analyte detection systems using responsive polymer-coated magnetic nanoparticles and non-agglomerative bioanalytical assays.

BACKGROUND OF THE INVENTION

Biocompatible magnetic nanosensors have been designed to detect molecular interactions in biological media. Upon target binding, magnetic nanosensors cause changes in spin-spin relaxation times of neighboring water molecules (or any solvent molecule with free hydrogens) of a sample, which can be detected by classical magnetic resonance (NMR/MRI) techniques. By using nanosensors in a sample, it is possible to detect the presence of an analyte at very low concentration—for example, small molecules, specific DNA, RNA, proteins, carbohydrates, lipids, lipoproteins, organisms, and pathogens (e.g. bacteria, viruses, etc.)—with sensitivity in the low femtomole range (e.g., about 0.5 fmol to about 30 fmol per microliter; less than ten analyte particles (e.g., virus/cell) per microliter).

In general, magnetic nanosensors used are superparamagnetic nanoparticles functionalized with affinity moieties that bind or otherwise link to their intended molecular target to form clusters (aggregates) or nanoassemblies. It is thought that when superparamagnetic nanoparticles assemble into clusters and the effective cross sectional area becomes larger, the nanoassembly becomes more efficient at dephasing spins of surrounding water (or other solvent) protons, leading to an enhancement of measured relaxation rates (1/T2). Additionally, nanoassembly formation can be designed to be reversible (e.g., by temperature shift, chemical cleavage, pH shift, etc.) so that "forward" or "reverse" assays can be developed for detection of specific analytes. Forward (clustering) and reverse (declustering) types of assays can be used to detect a wide variety of biologically relevant materials. Furthermore, spin-lattice relaxation time (T1) is considered independent of nanoparticle assembly formation and can be used to measure concentration in both nano-assembled and dispersed states within the same solution.

Examples of magnetic nanosensors are described in Perez et al., "Use of Magnetic Nanoparticles as Nanosensors to Probe for Molecular Interactions," *ChemBioChem,* 2004, 5, 261-264, and in U.S. Patent Application Publication No. US2003/0092029 (Josephson et al.), the texts of which are incorporated by reference herein, in their entirety. Examples of magnetic nanosensors include monocrystalline iron oxide nanoparticles from about 3 to about 5 nm in diameter surrounded with a dextran coating approximately 10 nm thick such that the average resulting particle size is from about 25 to about 100 nm. Another example of magnetic nanosensors include polycrystalline iron oxide nanoparticles of about 100 nm to about 1 micron in diameter.

Nanosensors have demonstrated low femtomolar analyte detection sensitivity through cluster formation (i.e. aggregation) and dispersion (i.e. disaggregation) assays. However, sensivity is just one requirement for a versatile bioanalytical detection system. A versatile bioanalytical detection system should also provide rapid results and be adaptable to functioning with a wide range of analyte concentrations for a variety of bioanalytical assays. Aggregation/disaggregation of nanosensors may not be the optimal method for analyte detection in all assays.

For example, cluster formation can only occur when each nanoparticle is bound to multiple analytes and, in some cases, each analyte is bound to multiple nanoparticles. Additionally, aggregation can be inhibited by geometrical effects such as a variation in size among nanosensors and analytes. Further, long incubation time may be required for cluster formation due to a two-step kinetic process for aggregation. Analyte needs to first bind to one or more nanosensor(s), then nanosensors agglomerate with each other to form clusters.

Cluster formation has also been shown to limit the dynamic range for certain bioanalytical assays. Factors that may contribute to limiting dynamic range include the structural instability of clustered aggregates. In addition, excess aggregation may lead to precipitation of nanosensors out of solution. Further, imperfect magnetization coupling of nanoparticles with each other, over an extended period of incubation time, may also contribute to a reduction in net magnetization per unit volume of a cluster, making relaxation process less efficient and lowering its magnitude. Therefore, the need exists for designs of versatile nanosensors and bioanalytical assays that exploit the individual magnetic nanoparticle's enhanced capability of dephasing spins of water protons for analyte detection without aggregation.

SUMMARY OF THE INVENTION

Provided methods and compositions exploit the ability of magnetic nanosensors to dephase nuclear spins, hereinafter generally exemplified as protons of water molecules, detectable by nuclear magnetic resonance (NMR) relaxation measurements (e.g., $1/T_2$), for sensing and/or measuring an analyte of interest, without aggregation of nanosensors. In principle, $T_2$ relaxivity of water protons dephased by nanosensors can be proportional to the diameter of nanosensors present in a solution and the diffusion time of water protons in the proximity of individual nanosensors. Thus, provided compositions and bioanalytical assays comprise magnetic nanosensors introduced into a sample that may contain a target analyte in order to react with target analyte in a sample in a rapid, and homogeneous reaction. Provided bioanalytical assays include compositions and methods for optimizing the size or responsive size of nanosensors, to enable rapid assay time-to-results, increased sensitivity, and large (e.g., wide) relaxivity (e.g., $T_2$) dynamic range.

Provided are nanosensors that exploit the ability of magnetic nanoparticles to dephase nuclear spins detectable by NMR, for detection without aggregation of nanoparticles. In particular embodiments, provided nanosensors comprise a nanoparticle having a polymer matrix layer which responds (e.g., expands or contracts) when exposed to an analyte and/or a condition to be detected. A resulting change in nanoparticle size affects dephasing of freely-diffusing water molecules in the vicinity of the nanoparticles, which affects one or more NMR-detectable properties.

In other particular embodiments, provided nanosensors comprise a nanoparticle having a binding agent which is size optimized to provide optimal $T_2$ measurement. A resulting change in nanoparticle size when exposed to an analyte and/or a condition to be detected provides a maximum change in $T_2$.

Additionally provided are particular methods of using provided responsive nanosensor compositions, wherein NMR-detectable properties can be obtained using responsive nanosensor compositions to determine the existence and/or level of a condition and/or analyte of interest in one or more samples. In certain embodiments, comparing obtained NMR-detected properties with a known control (e.g., one or more reference samples, a known control reference measure), may determine the existence and/or level of a condition and/or analyte of interest in one or more samples.

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout various views.

While the present invention is particularly shown and described herein with reference to specific examples and specific embodiments, it should be understood by those skilled in the art that various changes in form and detail may be made therein without departing from the spirit and scope of the invention.

BRIEF DESCRIPTION OF THE DRAWING OF THE INVENTION

FIG. 1 is a schematic depicting a principle of operation and elements of a responsive polymer (e.g., matrix) coated nanosensor, according to an illustrative embodiment of the invention. FIG. 1a is schematic of a region of the matrix, depicting binding moieties of a responsive polymer coated nanosensor in one state (e.g., before stimulus). FIG. 1b is schematic of a region of the matrix depicting binding moieties of a responsive polymer coated nanosensor in another state (e.g., after stimulus).

FIG. 2 is a schematic similar to FIG. 1, wherein the matrix takes the form of a membrane containing plural magnetic particles, according to an illustrative embodiment of the invention. FIG. 2a is schematic of a small region of the matrix depicting binding moieties of a responsive polymer coated nanosensor in one state (e.g., before stimulus). FIG. 2b is schematic of a small region of the matrix depicting binding moieties of a responsive polymer coated nanosensor in another state (e.g., after stimulus).

FIG. 3 is a schematic that depicts a principle of operation and device elements of a responsive polymer coated nanosensor for non-competitive affinity reactions, according to an illustrative embodiment of the invention. FIG. 3a is schematic of a region of a matrix depicting binding moieties of a responsive polymer coated nanosensor for non-competitive affinity reactions in one state (e.g., before stimulus). FIG. 3b is schematic of a region of amatrix depicting binding moieties of a responsive polymer coated nanosensor for non-competitive affinity reactions in another state (e.g., after stimulus).

FIG. 4 is a schematic that depicts a principle of operation and device elements of a responsive polymer coated nanosensor for competitive affinity reactions, according to an illustrative embodiment of the invention. FIG. 4a is schematic of a region of amatrix depicting binding moieties of a responsive polymer coated nanosensor for competitive affinity reactions in one state (e.g., before stimulus). FIG. 4b is schematic of a small region of amatrix depicting binding moieties of a responsive polymer coated nanosensor for non-competitive affinity reactions in another state (e.g., after stimulus).

FIG. 5 is a schematic that depicts a principle of operation and device elements of a responsive polymer coated nanosensor configured with multiple binding moieties, according to an illustrative embodiment of the invention. FIG. 5a is schematic of a small region of matrix, illustrating binding moieties of a responsive polymer matrix coated nanosensor configured with multiple binding moieties in one state (e.g., before stimulus). FIG. 5b is schematic of region of a matrix, illustrating binding moieties of a responsive polymer matrix coated nanosensor configured with multiple binding moieties in one state (e.g., after stimulus).

FIG. 10 depicts theoretical and actual results of experiments determining the effect of T2 measurements on nanosensor size. FIG. 10A depicts the theoretical shift in T2 obtained by increasing the size of a nanosensor by coating it with an antibody. As more antibodies are titrated in to the reaction and more nanoparticles become saturated with antibody, measured T2 decreases in response to the increased size of antibody-bound nanosensor. FIG. 10B depicts experimental results of T2 measurements of identically prepared nanoparticles with increasing levels of bound antibody or antibody conjugated to a large protein (alkaline phosphatase).

Figure 11A:
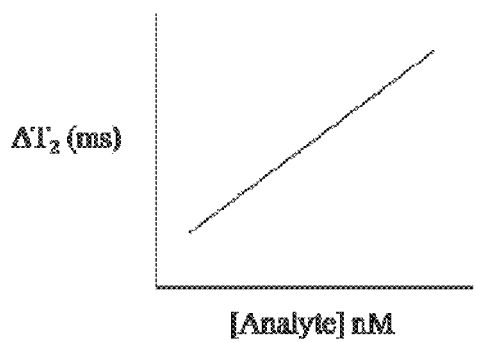
Figure 11B:
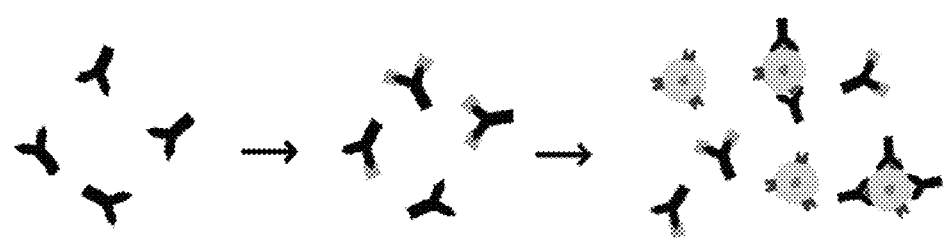

FIG. 11 depicts positive correlation between results obtained using provided methods and FIG. 11A depicts results demonstrative positive correlations between measured T2 and analyte concentrations for each of provided dispersive competitive assays and provided inhibitive competitive assays. FIG. 11B depicts a schematic of a two step inhibitive assay as a preferred format for competitive assay method.

Figure 12A:
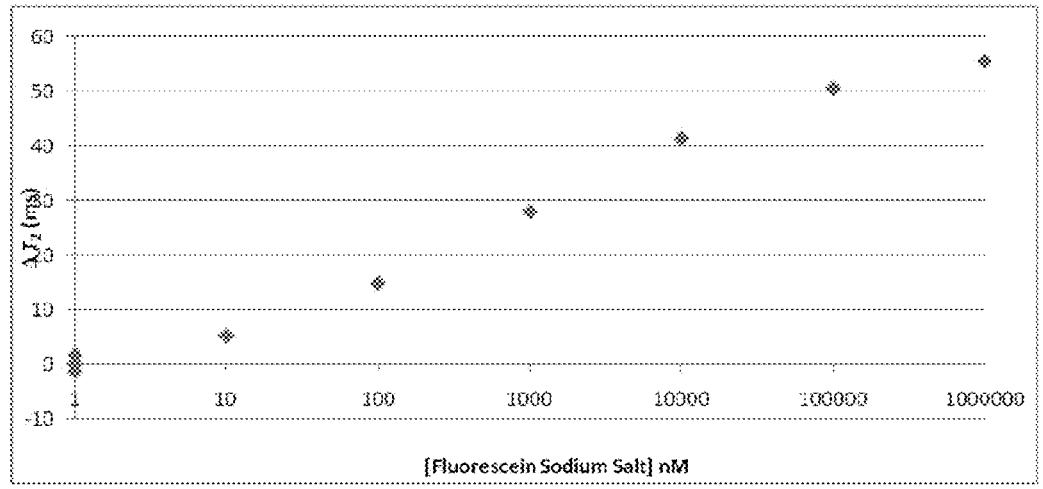
Figure 12B:
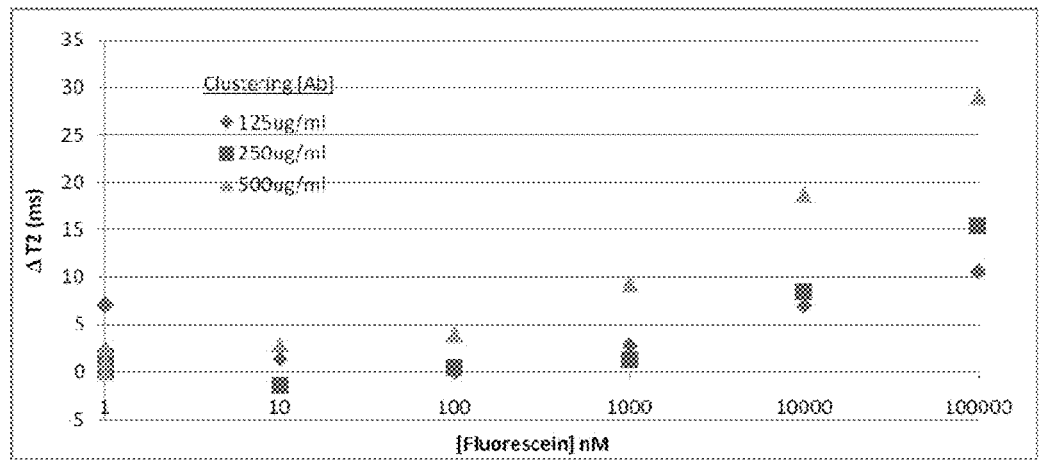

FIG. 12 depicts results of competitive nanosensor assays according to the invention. FIG. 12A depicts results of dispersive competitive assays; and FIG. 12B depicts results of inhibitive competitive assays.

DETAILED DESCRIPTION OF CERTAIN EMBODIMENTS OF THE INVENTION

It is contemplated that devices, systems, methods, and processes of the claimed invention encompass variations and adaptations developed using information from the embodiments described herein. Adaptation and/or modification of the devices, systems, methods, and processes described herein may be performed by those of ordinary skill in the relevant art.

Throughout the description, where devices and systems are described as having, including, or comprising specific components, or where processes and methods are described as having, including, or comprising specific steps, it is contemplated that, additionally, there are devices and systems of the invention that consist essentially of, or consist of, the recited components, and that there are processes and methods according to the invention that consist essentially of, or consist of, the recited processing steps.

As used herein, an analyte (or target analyte) may include one or more species of one or more of the following: a protein, a peptide, a polypeptide, an amino acid, a nucleic acid, an oligonucleotide, a therapeutic agent, a metabolite of a therapeutic agent, RNA, DNA, an antibody, an organism, a virus, bacteria, a carbohydrate, a polysaccharide, and glucose. An analyte may also include, for example, a lipid, a gas (e.g., oxygen, carbon dioxide), an electrolyte (e.g., sodium, potassium, chloride, bicarbonate, BUN, creatinine, glucose, magnesium, phosphate, calcium, ammonia, lactate), a lipoprotein, cholesterol, a fatty acid, a glycoprotein, a proteoglycan, and/or a lipopolysaccharide. Furthermore, as used herein, "detection of (an) analyte" may also mean measurement of physical properties of a solution containing one or more analytes, for example, measurement of dipole moment, ionization, solubility/saturation, viscosity, gellation, crystallization, and/or phase changes of the solution.

In certain embodiments, a parameter of the environment to be detected is the concentration of one or more analyte(s) in the environment (e.g. in a liquid sample), where an analyte can be, for example, a protein, lipid, a gas (e.g., oxygen, carbon dioxide), an electrolyte (e.g., sodium, potassium, chloride, bicarbonate, BUN, creatinine, glucose, magnesium, phosphate, calcium, ammonia, lactate), a lipoprotein, cholesterol, a fatty acid, a glycoprotein, a proteoglycan, a lipopolysaccharide, a peptide, a polypeptide, an amino acid, a nucleic acid, an oligonucleotide, a therapeutic agent, a metabolite, a metabolite of a therapeutic agent, RNA, DNA, an antibody, an organism, a virus, a bacteria, a pathogen, a carbohydrate, a polysaccharide, and/or glucose. Alternatively, a parameter of the environment to be detected may be a static or dynamic pH or ionic strength of a sample solution. The parameter may also be a thermal, mechanical, electromechanical, electric, magnetic, acoustic, or optical stimulus. In other embodiments, the parameter is ionizing or non-ionizing radiation, an enzymatic reaction, a catalytic reaction, an acidic or basic stimulus, or a change in lipophilicity, hydrophobicity, or hydrophilicity.

As used herein, one or more binding moieties, binding pairs, or binding pendants may broadly be a chemical binder, an electroactive mediator, an electron-pair donor, and/or an electron-pair acceptor. A binding moiety may include one or more species of one or more of the following: an atom, an ion, a molecule, a compound, a catalyst, an enzyme, an electroactive mediator, an electron-pair donor, an electron-pair acceptor, a lanthanide, an amino acid, a nucleic acid, an oligonucleotide, a therapeutic agent, a biological molecule, a metabolite of a therapeutic agent, a peptide, a polypeptide, a protein, a carbohydrate, a polysaccharide. Binding moieties may be a polymer, or may be part of a polymer that is linked to magnetic particle. Alternatively, a binding moiety-target can be binding pairs, or binding pendants, such as antibodies and cognate antigens. For example, a binding moiety-target may be avidin-biotin or a ligand binding protein such as concanavalin A with affinity for a carbohydrate. Examples of the combination of a binding moiety and a target thereto include combinations of antigen and antibody, a certain saccharide and lectin, biotin and avidin, protein A and IgG, hormone and receptor thereof, enzyme and substrate, and nucleic acid and complementary nucleic acid or in each case, vice versa. In certain embodiments, binding moieties may include one, two, or more types of oligonucleotides and/or one, two, or more types of proteins, etc. Biological molecules include binding agents or target molecules of biological origin or synthetically made molecules that mimic the performance of biological molecules. Examples include, but are not limited to, peptides with non-natural amino acids, peptide nucleic acids (PNA's), or natural or man-made organic molecules that react with specific sites on target biological molecules. In certain embodiments, the target analyte molecule is a nucleic acid, and each binding moiety includes one of two or more different oligonucleotides, wherein each oligonucleotide is complementary to a region on the target nucleic acid that is different than the regions to which the other oligonucleotides are complementary. In other embodiments, a target molecule can be a polypeptide, and each binding moiety includes one of two or more different antibodies, wherein each antibody specifically binds to a binding site on the polypeptide that is different than the binding sites to which the other antibodies bind. In some embodiments, binding moieties bind to each other including one or more antigen(s) with one or more antibody(ies) having affinity for the one or more specific antigen(s). In some embodiment an antibody is a monoclonal antibody or antigen binding fragment thereof. A binding moiety can include a cleavage site that is selectively cleaved by a target molecule, and cleavage of the binding moiety results in separation of the cross-link. Alternatively, the binding moieties can be polypeptides and the target molecule can be an enzyme. In other examples, each binding moiety can bind to another binding moiety to form a cleavage site that is selectively cleaved by a target molecule, and cleavage of the binding moiety results in separation of the cross-link. Further, a target can be a virus, virus components (i.e. capsids), a cell, components of cells (e.g., vesicles, apoptotic bodies, organelles, cell debris/dead cells), and other particles (e.g., circulating clots, cholesterol particles, plaques, forms of amyloid, and micelles). A cell can be a prokaryotic cell such as bacteria or a eukaryotic cell such as mammalian cell including cells of a human organ. A target can be also be a surface antigen, a G-protein receptor, a polysaccharide, or any atom, ion, or molecule that antibody can be produced using known immunological methods. Binding moieties preferably include functional groups for attachment to a substrate or surface. For example, the binding moieties can include one or more species of one or more of the following: an amino group, a carboxyl group, a sulfhydryl group, an amine group, an imine group, an epoxy group, a hydroxyl group, a thiol group, an acrylate group, and/or an isocyano group or a mixture thereof.

As used herein, "container" is understood to mean any localizer of a liquid sample, for example, a well, or an indentation, or a support, or a channel, or a reservoir, or a sunken volume, or a compartment, or a recessed area, or an enclosure with or without an opening, or a tube, or a trough. At least one surface of the container can be, but is not necessarily, functionalized with one or more types of binding moieties.

As used herein, nanosensors, functionalized nanosensors or magnetic nanosensors mean magnetic (e.g., paramagnetic, superparamagnetic) nanoparticles, optionally functionalized with one or more binding moieties. Each species of functionalized nanosensor used in a composition or assay described herein can have unique characteristics including the size of the nanosensors and the type of magnetic material(s) and coating used. Nanosensors can be functionalized with binding moieties attached to their surfaces as described in further detail herein. A magnetic core of the nanoparticles is preferably nanometer scale (for example, less than about 100 nm in diameter) and is preferably paramagnetic or superparamagnetic. A core of the nanoparticles may be fabricated using known techniques from any type of magnetic, paramagnetic, or superparamagnetic nanometer-scale metal core including an oxide and/or a hydroxide of Fe, Si, Sn, An, Ti, Bi, Zr, and/or Zn. Magnetic particles can be composed of single metal crystals or of multiple metal crystals. Magnetic nanoparticles include, for example, superparamagnetic particles, paramagnetic particles, and/or magnetic particles, with sizes, for example, of less than about 1 µm in at least one dimension (e.g., diameter), less than about 500 nm in at least one dimension (e.g., diameter), less than about 400 nm in at least one dimension (e.g., diameter), less than about 300 nm in at least one dimension (e.g., diameter), less than about 200 nm in at least one dimension, 100 nm in at least one dimension (e.g., diameter), less than about 60 nm, less than about 50 nm, less than about 40 nm, less than about 30 nm, less than about 20 nm, less than about 10 nm, or less than about 5 nm in at least one dimension Magnetic nanoparticles used in particular embodiments have a metal oxide core of about 1 nm to about 25 nm, from about 3 to about 10 nm, or about 5 nm in diameter. Magnetic particles used in particular embodiments are superparamagnetic and have crystalline core size from about 1 nm to about 100 nm.

Magnetic Resonance

A brief summary of the technical elements relating to the principles of the invention are provided herein. Nanosensors are introduced into a sample, preferably a liquid such as water, which has an atomic nucleus that has a non-zero spin, such as hydrogen. As is well known in the art, a magnetic component of such a nucleus becomes polarized or spatially oriented in a bias magnetic field, and may be induced into magnetic resonance precession at the Larmor frequency. Magnetic components, or magnetic moments, of nuclei are vector quantities and add together to give a resultant bulk magnetization vector that is the NMR signal measured by NMR spectrometers.

When in proximity of individual magnetic nanosensors, water protons interact with nanosensors and their magnetic field gradient through translational and rotational diffusion, predominantly translational. Prolonged interaction of water protons with individual nanosensors translates to an enhanced dephasing of water protons, and thus changes in $T_2$ relaxivity. In general, in an NMR detector (e.g., a conventional magnetic relaxometer equipment or an apparatus specially designed for MR detection), an external bias magnetic field is applied to a sample comprising nanosensors. Before, during, and/or after a mixing and/or incubation period, one or more radio frequency pulses, preferably at or about the Larmor frequency, are applied to stimulate water protons in the proximity of nanosensors. $T_2$ relaxivity of nuclei can be detected and processed and, in some embodiments, compared to a standard or control sample. $T_2$ relaxivity measurements using MR detectors are used to detect the nanosensors. Such measurements may allow for determination of the presence and/or amount or concentration of a target analyte.

Following a perturbation such as that employed in recording NMR signals, a bulk magnetization vector recovers to its original steady state over time. This process is referred to as nuclear magnetic relaxation. There are two fundamental time constants that can be measured for the relaxation process. Recovery of bulk magnetization along the direction of the bias magnetic field is described by spin-lattice relaxation time or longitudinal relaxation time, designated as $T_1$. Typically, $T_1$ is on the order of milliseconds to seconds. The single-exponential decay of bulk magnetization in the plane perpendicular to the direction of the first magnetic field is described by the spin-spin relaxation time, or transverse relaxation time, designated as $T_2$. For liquid signals, $T_2$ is generally in the range of 100 milliseconds or more.

A magnetic resonance measurement can be performed by applying one or more RF (radio frequency) energy pulses to a sample and measuring bulk magnetization that becomes reoriented by the pulse. RF pulses have a frequency equal to the Larmor frequency, and duration sufficient to cause a bulk magnetization vector to reorient into a plane perpendicular to the bias magnetic field, where the bulk magnetization vector (the NMR signal) can be recorded over time. The most common method to measure spin-spin relaxation is that originally described by Can and Purcell and later modified and known in the art as the Carr-Purcell modified Meiboom-Gill (CPMG) method.

A model can provide a framework for general working principles of the invention, more specifically for quantifying and maximizing $T_2$ relaxivity. A simplified nanoparticle is assumed to comprise a core (e.g., a spherical core) of superparamagnetic material, surrounded by a shell (e.g., a spherical shell) of non-magnetic material, all in water. The model can be applied or modified for use with nanoparticles of a variety of shapes, as well as for use with alternative solvents (e.g., sample comprising hydrogen nuclei). Nanosensors in solution reduce a $T_2$ time constant relative to plain water. The depolarization of a water proton is due to a dipole magnetic field produced by a magnetized core of nanosensors. Field distortion causes spins to process at different frequencies, leading to destructive interference. Although a CPMG method normally refocuses static field-nonuniformity effects, Brownian motion of water protons causes them to enter and exit field distortions in a time shorter than echo interval, thereby making spin dispersion time-dependent and breaking the CPMG refocusing effect. The $T_2$ relaxivity of water protons depolarized by nanosensors are proportional to the specific volume fraction of nanosensors present in a solution, and the diffusion time of the water protons in the proximity of individual nanosensors. $T_2$ relaxivity observed for a solution in the proportionality is:

$$1/T_2 \alpha (V_p)(R^2/D)$$

where $V_p$ is the specific volume fraction of the particles in solution, R the radius of the nanosensors particles, and D the diffusion constant of water. The term $R^2/D$ is equal to diffusion time, $\tau_d$. This is the time duration for a water molecule to diffuse within the dipole magnetic field produced by the magnetized core of the nanosensors, and is proportional to the extent of $T_2$ relaxation that occurs.

Certain aspects of the invention comprise bioanalytical assays configured for rapid reaction kinetics and high dynamic range MR detection. Provided bioanalytical assays can be used to assess the presence and/or amount or concentration of a target analyte in a sample.

In certain embodiments, provided methods utilize superparamagnetic nanosensors, a sample that may contain a target analyte, and a sample (e.g., an aqueous sample), which provides protons (e.g., hydrogen protons) that emit magnetic resonance signals. In particular embodiments a sample may be a fluid sample, including, e.g., water, saline, buffered saline, or a biological fluid. In certain embodiments a sample includes a biological fluid selected from one or more of blood, a cell homogenate, a tissue homogenate, a cell extract, a tissue extract, a cell suspension, a tissue suspension, milk, urine, saliva, semen, and/or spinal fluid.

Magnetic resonance signals can be influenced by diffusion, particularly diffusion of water protons and diffusion of the nanosensors in a sample. Magnetic resonance measurements can also be influenced by spin diffusion, a phenomenon in which the spin or polarization of a nucleus is interchanged with that of a nearby nucleus of the same type. Spin diffusion can distribute spin-dependent effects, such as depolarization, throughout the sample. For example, if a small fraction of hydrogen nuclei in water experience a depolarizing force, spin diffusion can cause all of the hydrogen in the sample to assume an averaged polarization value.

In certain embodiments, nanosensors used in conjunction with provided methods are superparamagnetic nanoparticles that produce high perturbations of the bias magnetic field in a region close to the nanoparticles. A paramagnetic or superparamagnetic core of a nanoparticle becomes magnetized when an external bias magnetic field is applied to it. A superparamagnetic core exhibits a high permeability, but little or no hysteresis. When placed in a magnetic field, a core becomes strongly magnetized parallel to the direction of the applied field, then loses essentially all of its magnetization upon removal of the external magnetic field. A magnetized core produces a magnetic field which usually approximates a dipole field, or the magnetic field produced by an ideal magnetic dipole located at the center of the paramagnetic core of the nanoparticle. The dipole field adds linearly to the applied field (as vectors), resulting in a net magnetic field or net magnetization. The Larmor frequency is determined by a net magnetic field experienced by polarized nuclei or water protons. In general, nanosensors, and derivatives thereof known in the art may be adapted according to the description herein for production of compositions and use in conjunction with provided methods.

In general, the functionalized nanosensors are contacted with a sample that may contain a target analyte in a container. Either the original container containing the reagent(s) or a new container to which the reagents and sample have been transferred is placed within a RF coil of a NMR detector. An RF frequency is tuned to the appropriate wavelength as dictated by the strength of the magnetic field and gyromagnetic ratio of the detected nuclei. RF excitation pulses are product by a spectrometer and transferred to the RF coil which has been placed in the proximity of the container. These pulses, such as 90° or 180° pulses, generate signals, such as echoes, from the solvent (water) protons. The detected signal is influenced by the superparamagnetic nanoparticles that couple the magnitude or type of influence to the amount, concentration, or presence of the target analyte in the sample. The presence, amount and/or concentration of the target analyte in a biological fluid sample can then be determined from the detected RF signal(s).

Provided aspects of the invention comprise bioanalytical nanosensor coating assays configured for improved sensitivity, high dynamic range and improved diagnostic assay MR detection. Provided bioanalytical assays can be used to assess the presence and/or amount and/or concentration of analyte in a sample.

In prior work, methods of nanosensor based MR assays for detection of analyte comprise addition of reagents to a sample which results in formation of an ensemble of clusters of varying sizes, leading to measurable changes in relaxation rates (e.g., T2). Parameters of such assays can be tuned to favor cluster formation of specific sizes. Such approaches have relied on reaching a dynamic equilibrium and kinetics during nanoparticle self assembly; however, such methods can result in over titrated assay configurations, leading to nanoparticle destabilization (Kim et al, 2007; Taktak et al 2007; Lowery et al 2007; Kim et al 2008). Resulting destabilization can limit an overall dynamic range of an assay, as well as lead to polydisperse mixtures of nanoparticle clusters, which may decrease the overall change in T2 relaxation rates in a sample, resulting in inaccurate detection measurements. Additionally, in the classic MRSw design, resulting nanoparticle binding agent clusters can be of varying size. Control of the resulting solution (e.g., cluster formation, cluster stability), though possible, can be challenging. Under a given set of assay conditions (e.g., iron concentration, temperature, basic nanoparticle size, diffusivity, inter-echo delay, etc), there is a decrease in T2 signal as cluster size increases from <100 nm to ~100 nm. Above ~100 nm, T2 signal begins to rise. Therefore, when cluster formation is uncontrolled, it is difficult to ensure that a maximal ΔT2 signal is being achieved with a change in cluster size, as the change in size may be moving the T2 in more than one direction, resulting in a decreased absolute ΔT2.

Provided methods comprise competitive assays, including competitive dispersive assays where analyte bound nanoparticles (e.g., nanoparticles decorated with analyte or analyte surrogate (e.g., analog)) are complexed in the presence of a binding agent (e.g., an antibody) prior to being challenged with sample; and inhibitive coating assays where sample is pre-incubated with a binding agent (e.g., an antibody) prior to being challenged with analyte bound nanoparticles (e.g., nanoparticles decorated with analyte or analyte surrogate (e.g., analog)).

Provided methods comprise addition of a binding agent to a single population of analyte-bound nanoparticles. The method involves coating a nanoparticle with a single layer of analyte, and a single layer of binding agent. Based on size measurements, the layer of binding agent is formed even if the binding agent is divalent (e.g., IgG antibodies). Addition of binding agent in this assay format leads to a uniform increase in size among all nanoparticles. This size increase is only dependent on concentration of binding agent and on the size of the binding agent and analyte, which are both highly adjustable. We hypothesize that this layer formation is thermodynamically and sterically favorable over cluster formation. Further, provided methods result in formation and assay of a single population of non-aggregated nanosensors, thereby allowing for optimized and accurate measurements of relaxation parameters.

Provided are methods wherein size of complexes formed upon addition of binding agent and/or target analyte is inherently limited by design of the assay reagents, and wherein thermodynamically and sterically favorable single, non-aggregated nanosensors coated with binding agent are formed. Provided methods reduce the polydispersity of nanosensor solution after addition of analyte in favor of formation of binding agent coated single nanosensor, thereby optimizing delta T2 measurements. With this approach, complexes formed by addition of analyte are limited by the available binding sites and the size of the binding agent, which is inherently easier to control and optimize rather than the thermodynamics and kinetics of the clustering process. Provided methods allow the ability to directly control complex formation (and detection measurements) through the architecture of assay reagents.

In certain embodiments, provided methods utilize superparamagnetic nanosensors, one or more binding agent(s), and a sample (e.g., an aqueous sample) that may contain analyte and which provides protons (e.g., hydrogen protons) that emit magnetic resonance signals. Magnetic resonance signals can be influenced by diffusion, particularly diffusion of water protons and diffusion of the nanosensors in a sample.

In certain embodiments, nanosensors are used in conjunction with provided methods in a manner similar to those generally known in the art and generally described herein, with particular selection of reagents to optimize for robust and controllable MR measurements through use of provided nanosensor coating assays. In general, nanosensors, and derivatives thereof known in the art may be adapted according to the description herein for production of compositions and use in conjunction with methods of measurement of relaxation. Additionally, or alternatively, provided transducers comprising nanosensors having responsive polymer coatings, as well as provided MRSw coating assay compositions may be adapted (independently or in conjunction) for use in conjunction with the present methods.

In particular embodiments, nanosensors are functionalized with one or more of a variety different types of binding moieties. Where more than one functionalized nanosensors are used in an assay described herein, each one used will preferably be functionalized with a binding moiety that has affinity for a different target than the other(s).

In one embodiment, a bioanalytical assay for the detection of one or more target analytes in a sample includes introducing one or more species of functionalized nanosensors into a sample, allowing functionalized nanosensors to interact with any target analyte(s) in the sample, measuring the change in T2 relaxivity and determining the presence, amount and/or concentration of the target analyte(s). As a result of interaction between binding moieties and target analyte, binding moieties bind to the target analyte, thereby producing (or dispersing) functionalized nanosensors comprising a monolayer coating of binding agent that partially or completely surrounds or coats the nanoparticle. As binding agent adds to or disperses from a monolayer coating of nanosensor(s), the effective size of the nanosensors change. These factors serve to produce a change in $T_2$ relaxivity that is proportional to an amount or concentration of the target analyte or that indicates the presence of the target analyte.

In certain embodiments methods comprise "coating" analyte-decorated nanoparticles with binding agents of known and controlled size. The size of the binding agent (e.g., an antibody) can be optimized by the addition of size increasing moieties of known size to a non-binding region of the binding agent. Optimization depends upon the sizes of magnetic nanoparticle being utilized, and any associated coating, as well as the analyte coating and the binding agent. Because the binding agent binds directly and exclusively to analyte coated particles, a maximum achievable diameter of the resulting particle is roughly 3 times the diameter of the individual nanoparticle, plus the lengths of the binding agent and any size altering body attached to it. Final cluster size can therefore be controlled directly by varying the initial nanoparticle size, analyte size, as well as by varying the size of any size modifying structure that may be attached to the binding agent. This gives the user direct control over the maximum final nanoparticle-binding agent complex size to ensure an optimal ΔT2 signal. This level of control was not possible during the formation of branching clustered structures formed using the traditional clustering method.

Certain embodiments comprise inhibitive coating assays where a sample is pre-incubated with a binding agent (e.g., an antibody) prior to being challenged with analyte bound nanoparticles (e.g., nanoparticles decorated with analyte or analyte surrogate (e.g., analog)). Preferably reagents are selected for formation of nanosensors capable of generating a maximal ΔT2 signal. This should significantly improve the dynamic range and sensitivity of nanosensor assays requiring competitive dispersion to detect analyte.

Some embodiments comprise ompetitive dispersive coating assays wherein bound binding agent-analyte coated nanoparticle nanosensors are pre-formed. Preferably reagents are selected for formation of nanosensors capable of generating a maximal ΔT2 signal. This should significantly improve the dynamic range and sensitivity of nanosensor assays requiring competitive dispersion to detect analyte.

Provided methods expand the number of potential assays that can be developed. Thus, provided methods have the potential to greatly improve the performance of a wide range of detection assays in terms of sensitivity and dynamic range, facilitating faster development times and improved diagnostic assay performance. In addition, competitive dispersive nanosensor assays can now be produced for target analytes that lack multi-valent binding agents. Competitive dispersive MRSw assays may be useful, and in certain instances required, when developing detection assays for monovalent targets. In certain embodiments the method comprises use of single valence binding agents (e.g., monoclonal antibody).

In general, functionalized nanosensors are contacted with a sample that may contain a target analyte in a container. Either an original container containing the reagent(s) or a new container to which the reagents have been transferred is placed within a RF coil of a NMR detector. An RF frequency is tuned to the appropriate wavelength as dictated by the strength of the magnetic field and gyromagnetic ratio of the detected nuclei. RF excitation pulses are product by a spectrometer and transferred to the RF coil which has been placed in the proximity of the container. These pulses, such as 90° or 180° pulses, generate signals, such as echoes, from the solvent (water) protons. The detected signal is influenced by the superparamagnetic nanoparticles that couple the magnitude or type of influence to the amount, concentration, or presence of the target analyte in the sample. The presence, amount and/or concentration of the target analyte in a biological fluid sample can then be determined from the detected RF signal(s).

Provided bioanalytical assays may be used to assess the presence, amount and/or concentration of a variety of different types of target analytes, including proteins, lipids, electrolytes and related clinical chemistry analytes (e.g., sodium, potassium, chloride, bicarbonate, BUN, creatinine, glucose, magnesium, phosphate, calcium, ammonia, lactate), lipoproteins, cholesterol, fatty acids, glycoproteins, proteoglycans, lipopolysaccharides, peptides, polypeptides, amino acids, nucleic acids, oligonucleotides, therapeutic agents, metabolites, metabolites of therapeutic agents, RNA, DNA, antibodies, organisms, viruses, viral capsids, bacteria, pathogens, prions, carbohydrate such as polysaccharides or monosaccharides, human cells, vesicles, apoptotic bodies, organelles, cell debris, cell clots, amyloid, micelles, and various other biological molecules. Biological molecules can be either molecules of natural biological origin or synthetically made molecules that can, in some way, mimic the performance of biological molecules. Examples of such synthetic biological molecules include peptides with non-natural amino acids, peptide nucleic acids (PNA's), or natural or man-made organic molecules that react with specific sites on target biological molecules.

In certain embodiments, a target analyte can be a nucleic acid and the binding moiety can be an oligonucleotide that is complementary to a region on the target nucleic acid. In other embodiments, a target analyte can be a polypeptide and a binding moiety can be an antibody that specifically binds to a binding site on the polypeptide. Alternatively, binding moieties can be polypeptides and a target analyte can be an enzyme. In yet another embodiments, provided bioanalytical assays can be used for detection and/or differentiation of normal cells, abnormal cells (e.g., diseased cells, infected cell, tumor cells) and their subpopulation using binding moieties for specific surface markers.

In certain embodiments methods for detection of an analyte in a sample are provided. In some embodiment, the method comprises providing nanosensors and providing a fluid sample. The nanosensors comprise magnetic nanoparticles linked to an analyte or analog thereof. The nanosensors further comprise one or more binding moieties optionally linked to the analyte or analog thereof. The binding moieties are responsive to the analyte or analog thereof bound to the nanoparticle, as well as to analyte present in the sample. The nanosensor including analyte or analog thereof linked to the nanoparticle and binding moiety(ies) bound to analog are size optimized to confer optimal relaxation measurements. In some embodiments the method includes placing the sample and the nanosensors in a container under conditions and for a sufficient period of time to allow analyte in the sample to bind to and compete off the binding moiety from the analyte or analog thereof on the nanosensor; placing the container in proximity to an NMR detector; measuring one or more relaxivity parameters of the sample in the container; and determining one or more attributes relative to the sample.

In other embodiments methods for detection of an analyte in a sample are provided comprising providing a fluid sample and one or more binding moieties, the binding moieties responsive to a target analyte or analog thereof and placing the sample and binding moieties under conditions and for a sufficient period of time to allow analyte in the sample to bind to binding moiety. The methods further include providing nanosensors comprising magnetic nanoparticles linked to an analyte or an analog thereof, which analyte is responsive to the binding moieties incubated with the sample, and placing the pre-incubated sample and binding moiety(ies) and the nanosensors in a container under conditions and for a sufficient period of time to allow analyte linked to nanosensors to bind to and compete off the binding moiety from the analyte in the sample then placing the container in proximity to an NMR detector. Once placed in the detector, one or more relaxivity parameters of the sample in the container are measured, and one or more attributes relative to the sample are determined. The nanosensor including analyte or analog thereof linked to the nanoparticle and binding moiety(ies) bound to analog are size optimized to confer optimal relaxation measurements.

In some embodiments the attribute of a sample which is assessed or determined is any one or more of the presence of the analyte, the amount of the analyte and/or the concentration of the analyte in a sample. As discussed herein, in certain embodiment an analyte comprises at least one member selected from the group consisting of a protein, a peptide, a polypeptide, an amino acid, a nucleic acid, an oligonucleotide, a therapeutic agent, a metabolite of a therapeutic agent, RNA, DNA, an antibody, an organism, a virus, a bacteria, a carbohydrate, and a polysaccharide.

In certain aspects, a family of transducers for placement in an environment, e.g., for contact with a solution, typically an aqueous analyte solution are provided. When in an environment, provided transducers develop or display a proton or other nuclear spin relaxivity proportional to a physical parameter of the environment, or a component within the environment, which relaxivity is measurable from outside the solution using a magnetic reasonance detection device. Thus, contact of a transducer with an environment, such as a liquid sample containing an analyte of interest, and optional incubation to promote establishment of equilibrium between the environment and the transducer, permits indirect detection of the value of a preselected physical (including chemical) property of the environment and/or determination of the presence and/or concentration of a target molecule in the environment. The environment may be, for example, in vivo or ex vivo, where the environment contacting the transducer is a biological sample.

A transducer comprises one or more magnetic, e.g., paramagnetic or superparagmagnetic, particles having a polymer matrix layer containing one or more binding moieties. The binding moieties are responsive to the presence or concentration of an analyte in the environment and/or are responsive to some other property of the environment, such as, for example, static pH, dynamic pH, and/or ionic strength of the environment. The polymer matrix layer may partially or completely coat the magnetic core of each nanoparticle. The matrix may be, for example, a polymeric, hydrophilic, water-permeable hydrogel. In certain embodiments, the transducer operates by taking advantage of the dephasing of freely-diffusing water molecules in the vicinity of the responsive matrix layer of the nanoparticles. In the presence of an analyte or upon exposure to a condition to which the polymer matrix layer is responsive, the specific volume of the polymer matrix layer changes, leading to a detectable change in an NMR-measured property of protons in the environment of the nanoparticles(s). An NMR-measured property may be, for example, T1 and/or T2 relaxivity. For example, a change in T2 may be related to (1) a change in the magnetic particle size and (2) a change in the diffusion time of water (or other proton-containing molecules) in the vicinity of the particle, relative to particle size. Flux of water and/or other proton-containing molecules out of or into the matrix may also affect T2, but this effect may not be significant in light of (1) and (2). However, certain embodiments may take advantage of the effect on T2 (or other NMR-measured property) of the change in flux of proton-containing molecules out of or into the matrix, for example, in embodiments where magnetic nanoparticle cores are embedded in responsive polymer matrix material.

The transducer may take many geometric and chemical forms. It may take the form of a three dimensional mass of substrate material containing one or a plurality of polymer matrix-coated nanoparticles. The substrate may be in the form of a planar sheet or membrane. Preferably, the substrate does not significantly inhibit free diffusion of water molecules (or other proton-containing environmental molecules) about each polymer-coated nanoparticle. In certain embodiments, the nanoparticles are immobilized on a substrate surface by means of nonspecific absorption, specific chemical coupling, or specific binding of nanoparticle to substrate material. In certain embodiments, part of each nanoparticle is immobilized on the substrate surface while another part is free to interact with the sample environment (e.g., solution). The magnetic core of the nanoparticles are preferably nanometer scale (e.g., less than about 100 nm diameter, about 1 nm to about 100 nm) and are paramagnetic or superparamagnetic. The core of the nanoparticles advantageously may be fabricated using known techniques from any type of magnetic, paramagnetic, or superparamagnetic nanometer-scale metal core including an oxide and/or a hydroxide of Fe, Si, Sn, An, Ti, Bi, Zr, and/or Zn. In particular embodiments magnetic particles comprise single metal crystals; in other embodiments magnetic particles comprise multiple metal crystals. Magnetic nanoparticles preferably have a metal oxide core of about 1 to about 25 nm, from about 3 to about 10 nm, or about 5 nm in diameter. The responsive coating matrix may have a thickness in the range of 5 nm to 10,000 nm.

In a case where detected nuclei are water protons, a matrix preferably takes the form of a stimuli or molecule sensitive hydrogel comprising a polymer "mesh" that is cross-linked by binding moieties that affects the volume, permeability and the proton content of the matrix as a function of a physical or chemical stimulus or a physical parameter of the analyte under study. This is accomplished by design of the matrix as a hydrophilic polymer network comprising (as pendent groups or as part of the polymer backbone) binding moieties that influence water permeability (and/or permeability of other molecules in the environment) through formation of one or more covalent or hydrogen bonds, van der Waals interactions, or physical entanglement with a component of the analyte. The presence of analyte induces a change in the crosslink density of the polymer, which leads to a change in the volume fraction of the solution occupied by the polymer. The change in cross link density also leads to a change in the diameter of the nanoparticles, which leads to a change in their diffusion time. As discussed above, both diffusion time and specific volume are proportional to the $T_2$ relaxivity observed for a solution, as shown in the proportionality:

$$1/T_2 \alpha (V_p)(R^2/D)$$

where $V_p$ is the specific volume fraction of the particles in solution, R the radius of the particles, and D the diffusion constant of water. The term $R^2/D$ is equal to the diffusion time, $\tau_d$. This is the time necessary for a water molecule to diffuse past a particle, and is proportional to the extent of $T_2$ relaxation that occurs.

As discussed above, a binding moiety may broadly be a chemical binder, an electroactive mediator, an electron-pair donor, and/or an electron-pair acceptor. For example, the binding moiety may be an acetic acid moiety such as in poly(acrylic acid) for sensing pH, or phenylboronic acid for sensing the presence of diols, such as glucose Binding moieties may be antibodies that serve as cross-linkers in the presence of their cognate antigen, or antigens that serve as cross-linkers in the presence of their cognate antibodies, and which mediate the water proton flux in and out of the matrix and change in specific volume by competitive affinity reactions. This typically is accomplished as the extent of cross-linking of matrix polymer is mediated as a function of the physical parameter under study so as to control the permeability of water, including its amount and rate of translational diffusion in an out of the matrix and within the matrix volume in proximity to the magnetic particle(s). For example, the binding pairs may be a ligand binding protein such as concanavalin A bound to a low-affinity ligand such as a carbohydrate. Addition of glucose to this system would displace the low affinity ligand and change the crosslinking of the matrix. Another example is a matrix-immoblized antibody, antibody fragment, or peptide that crosslinks the matrix by binding to its matrix-immobilized antigen or target. The presence of a higher affinity analyte would lead to disruption of the cross-linked matrix and a swelling of the matrix.

Accordingly, provided are responsive polymer coated magnetic nanoparticle conjugates which behave as transducers and methods for their use. Each conjugate comprises a magnetic core covered at least partially with polymer matrix, e.g., a core embedded within a "matrix" or coated with a matrix or volume of water-permeable material whose level of association with nuclei and specific volume is responsive to the value of the physical or chemical parameter under study. The responsive matrix may comprise a matrix of material which includes one or more monomers and/or polymers. The one or more monomers and/or polymers contain functional groups that enable the binding moiety to be attached to or otherwise in stable association with the nanoparticle to form the conjugate. The polymer can be a natural polymer, a synthetic polymer, a combination of natural and synthetic polymers, shape memory polymers, block co-polymers (PEO, PPO), or derivatives of each type. For example, the matrix polymer may be poly (N-isopropylacrylamide). The matrix polymer may also be (or include), for example, Poly(N-isopropylacrylamide) (PNIAAm), Poly(N,N-diethyacrylamide) (PDEAAm), P(NIAAm-co-BMA), PEO-PPO-PEO (e.g., Pluronic®), N,N-diethylaminoethyl methacrylate (DEA), 2-hydroxypropyl methacrylate (HPMA), Poly-(methacrylic acid-g-ethylen glycol), Poly(2-glucosyloxyethyl methacrylate), Poly (N-vinyl-2pyrrolidone-co-3-(acrylamido)phenylboronic acid), and/or N—(S)-sec-butylacrylamide. Functional groups may comprise one or more appropriate chemical functional group(s), e.g. carboxy, amino, or sulfhydryl groups. A specific moiety or moieties may be attached to the nanoparticle via conjugation to these groups, or by physical adsorption and/or through hydrogen bonds or van der Waals interactions. The responsive polymer matrix, through physical and/or chemical stimuli, mediates the specific volume of the polymer layer, leading to a detectable change in NMR-measurable properties such as $T_2$ relaxivity. The NMR-measurable property(ies) may be related to the parameter(s) under study via one or more calibration curves using standards of known parameter value. The NMR-measurable property(ies) may include one or more discrete, continuous, differential, or integral measurements of the NMR relaxation rates $(1/T_1, 1/T_2)$ and may be measured with an NMR detector of the solute or solvent with susceptibility-induced dephasing by the magnetic nanoparticles. In particular embodiments a transducer conjugate can be used to measure any physical or chemical stimuli applied to the responsive polymer matrix. For example, the conjugate may be used for an assay for detecting a specific target molecule, such as a biological molecule in a sample solution or in vivo, by attaching one or more affinity moiety(ies) within the responsive polymer matrix with specificity for the target molecule. The conjugate may be used as a temperature sensor whereby thermal changes of the responsive polymer matrix result in changes of solvent flux or rate of change of flux as measured by changes in NMR relaxation rates $(1/T_1, 1/T_2)$. Thus, the new conjugate can be considered to be a responsive polymer matrix coated superparamagnetic nanosensor or nanotransducer outputting a relaxivity detectable by the antenna of a relaxometer that is related to the value of the parameter under investigation. In certain embodiments a responsive polymer matrix coated superparamagnetic nanosensor functions as a single entity, as a group of nanosensors; in other embodiments a responsive polymer matrix coated superparamagnetic nanosensor functions in an array of nanosensors, or in an encapsulation of nanosensors. Provided conjugate(s) may be incorporated with all embodiments and use for the detection of any of a wide variety of analytes as disclosed in copending U.S. patent application Ser. No. 11/513,503, filed Aug. 31, 2006, titled NMR DEVICE FOR DETECTION OF ANALYTES, the disclosure of which is incorporated herein by reference.

In one embodiment, each conjugate comprises a magnetic nanoparticle coated with a responsive matrix. The responsive matrix may be, for example, a polymeric, hydrophilic, water-permeable hydrogel. The responsive matrix contains one or more monomers or one or more polymers. The one or more monomer or one or more polymers contains one or more binding moieties, as described above, that determine the physical properties of the matrix including porosity and permeability through one or more covalent bonds, hydrogen bonds, van der Waals interactions, or physical entanglement of one or more binding moiety(ies). The one or more binding moiety(ies) mediates a swelling or shrinking of the polymer matrix, thereby leading to a change in $T_2$ by changing the specific volume of the particles or by changing the radius of the particles and thereby the diffusion time of the nuclei, and/or mediates a change in flux transport of solutes and solvent in and out of the responsive matrix; and, within the proximity of the magnetic nanoparticle and its magnetic field, magnetic field gradient when exposed to a magnetic field. The changes in matrix volume and/or changes in flux of solute or solvent, in and out of the responsive matrix, subsequently in and out of the magnetic field, magnetic field gradient of the nanoparticle, is proportional to the NMR relaxation rates ($1/T_1$, $1/T_2$) of the solute or solvent with susceptibility-induced dephasing by a magnetic nanoparticle. One or more discrete, continuous, differential, or integral NMR measurements are used to quantify one or more physical parameters, listed above, applied to the responsive matrix coated magnetic nanoparticle. Thus the responsive matrix coated magnetic nanoparticle is a nanosensor or a transducer for the applied physical or chemical stimuli (e.g., optical sensor, pressure sensor, etc.). The nanosensor may function as a single transducer for a specific stimulus or function simultaneously as a multiplex transducer with one or more nanosensors having sensitivities to different stimuli.

In another embodiment, magnetic nanoparticles each with one or more responsive polymer matrix layers are immobilized into or onto a substrate either randomly or in an ordered array. The responsive polymer membrane is a hydrogel that contains cross-linked polymers, cross-linked polymers attached to magnetic particles, and magnetic particles having polymer matrices with cross-linking binding moieties. The constituents of a hydrogel membrane including the cross-linking binding moieties determines its physical properties including porosity and permeability through one or more covalent bonds, hydrogen bonds, van der Waals interactions, or physical entanglement of one or more binding moiety(ies). The one or more binding moiety(ies), previously listed, mediates the flux transport of solutes and solvent of a solution in and out of a hydrogel membrane and within the proximity of one or more magnetic nanoparticle(s) and its (their) magnetic field(s), magnetic field gradient(s) when exposed to a magnetic field, effectively changing the particle's volume fraction. The shrinking or swelling of the polymer matrix, which leads to a change in specific volume or diffusion time of water and/or the changes in flux of solute or solvent, in and out of the polymer matrix, subsequently in and out of the magnetic field, magnetic field gradient of one or more nanoparticle(s) is proportional to the NMR relaxation rates ($1/T_1$, $1/T_2$) of the solute or solvent with susceptibility-induced dephasing by one or more magnetic nanoparticle(s). One or more discrete, continuous, differential, or integral NMR measurement(s) is (are) used to quantify the physical or chemical stimuli applied to a hydrogel membrane thus providing a transducer for the applied physical or chemical stimuli (e.g., optical sensor, pressure sensor, flow sensor etc.). A hydrogel membrane may function as a transducer for a specific stimulus or function as a multiplex transducer by incorporating one or more magnetic particles functionalized with sensitivities to different stimuli.

In another embodiment, each conjugate comprises a magnetic nanoparticle coated with a responsive polymer matrix. The responsive polymer matrix is a hydrogel that contains cross-linked polymers. A hydrogel contains one or more cross-linking binding moieties that are responsive to the pH or ionic strength or changes in pH or ionic strength of the solution, or the environment within a hydrogel, affecting one or more covalent bonds, hydrogen bonds, van der Waals interactions, or physical entanglement of a hydrogel. The one or more binding moiety(ies) responsive to the pH or ionic strength of the solution mediates the flux transport of solutes and solvent in and out of the hydrogel and within the proximity of the magnetic nanoparticle and its magnetic field, magnetic field gradient when exposed to a magnetic field. The shrinking or swelling of the polymer matrix, which corresponds to a change in specific volume and diffusion time, and/or the changes in flux of solute or solvent, in and out of the polymer coating, subsequently in and out of the magnetic field, magnetic field gradient of the nanoparticle is proportional to the NMR relaxation rates ($1/T_1$, $1/T_2$) of the solute or solvent with susceptibility-induced dephasing by a magnetic nanoparticle. One or more discrete, continuous, differential, or integral NMR measurements are used to quantify the pH or ionic strength of a solution containing one or more of the hydrogel coated magnetic nanoparticles.

In another embodiment, each conjugate comprises a magnetic nanoparticle coated with a responsive polymer matrix. The responsive polymer matrix is a hydrogel that contains cross-linked polymers. The hydrogel contains one or more binding moieties that generate a change in the pH or ionic strength of a solution, or the environment within the hydrogel, affecting one or more covalent bonds, hydrogen bonds, van der Waals interactions, or physical entanglement of the hydrogel, as a resultant of reaction with one or more specific analyte(s) present in a sample solution. The change in pH or ionic strength of the environment within the hydrogel mediates the flux transport of solutes and solvent in and out of the hydrogel and within the proximity of the magnetic nanoparticle and its magnetic field, magnetic field gradient when exposed to a magnetic field. The shrinking or swelling of the matrix, which correspond to a change in specific volume and/or diffusion time of the particles, and/or changes in flux of solute or solvent, in and out of the polymer coating, subsequently in and out of the magnetic field, magnetic field gradient of the nanoparticle is proportional to the NMR relaxation rates ($1/T_1$, $1/T_2$) of the solute or solvent with susceptibility-induced dephasing by a magnetic nanoparticle. One or more discrete, continuous, differential, or integral NMR measurements are used to quantify the amount or concentration of one or more analyte(s) present in the sample solution containing the hydrogel coated magnetic nanoparticles.

In another embodiment, each conjugate comprises a magnetic nanoparticle coated with a responsive polymer matrix. The responsive polymer matrix is a hydrogel that contains cross-linked polymers. The hydrogel contains one or more cross-linking binding moieties, or binding pairs, or binding pendants that determines its physical properties including porosity and permeability through one or more covalent bonds, hydrogen bonds, van der Waals interactions, or physical entanglement of one or more binding moieties, binding pairs, or binding pendants. The one or more binding moieties, binding pairs, or binding pendants mediates the shrinking or swelling of the polymer matrix and/or the flux transport of solutes and solvent in and out of the hydrogel and within the proximity of the magnetic nanoparticle and its magnetic field, magnetic field gradient when exposed to a magnetic field, through one or more competitive affinity reactions. The change in specific volume arising from shrinking or swelling and/or the flux or changes in flux of solute or solvent, in and out of the polymer coating, subsequently in and out of the magnetic field, magnetic field gradient of the nanoparticle is proportional to the NMR relaxation rates ($1/T_1$, $1/T_2$) of the solute or solvent with susceptibility-induced dephasing by a magnetic nanoparticle. One or more discrete, continuous, differential, or integral NMR measurements are use to quantify one or more analyte(s) present in the sample solution containing the hydrogel coated magnetic nanoparticles, the one or more analyte(s) that binds one or more binding moiety(ies), binding pairs, or binding pendants contained in the hydrogel.

In another embodiment, each conjugate comprises a magnetic nanoparticle coated with a responsive polymer matrix. The responsive polymer matrix is a hydrogel that contains cross-linked polymers. The hydrogel contains one or more cross-linking binding moieties, or binding pairs, or binding pendants that determines its physical properties including porosity and permeability through one or more covalent bonds, hydrogen bonds, van der Waals interactions, or physical entanglement of one or more binding moieties, binding pairs, or binding pendants. The one or more binding moieties, binding pairs, or binding pendants, listed above with alternative embodiments, mediates the flux transport of solutes and solvent in and out of the hydrogel and within the proximity of the magnetic nanoparticle and its magnetic field, magnetic field gradient when exposed to a magnetic field, through one or more non-competitive affinity reactions. The shrinking or swelling of the particle matrix and/or the flux or changes in flux of solute or solvent, in and out of the polymer coating, subsequently in and out of the magnetic field, magnetic field gradient of the nanoparticle, is proportional to the NMR relaxation rates ($1/T_1$, $1/T_2$) of the solute or solvent with susceptibility-induced dephasing by a magnetic nanoparticle. One or more discrete, continuous, differential, or integral NMR measurements are used to quantify one or more analyte(s) present in the sample solution containing the hydrogel coated magnetic nanoparticles, the one or more analyte(s) that binds one or more binding moiety(ies), binding pairs, or binding pendants contained in the hydrogel.

In another embodiment, each conjugate comprises a magnetic nanoparticle coated with a responsive polymer matrix. The responsive polymer matrix is a hydrogel that contains cross-linked polymers. The hydrogel contains one or more cross-linking reactive moiety(ies) that determines its physical properties including porosity and permeability through one or more covalent bonds, hydrogen bonds, van der Waals interactions, or physical entanglement of the one or more reactive moiety(ies). The one or more reactive moiety(ies) through a reaction with a reagent present in a sample solution mediates the flux transport of solutes and solvent in and out of the hydrogel and concomitant shrinking or swelling of the matrix that leads to a volume change within the proximity of the magnetic nanoparticle and its magnetic field, magnetic field gradient when exposed to a magnetic field, through one or more affinity reactions. The flux or changes in flux of solute or solvent, in and out of the polymer coating, subsequently in and out of the magnetic field, magnetic field gradient of the nanoparticle, and/or the change in specific volume of nanoparticles is proportional to the NMR relaxation rates ($1/T_1$, $1/T_2$) of the solute or solvent with susceptibility-induced dephasing by a magnetic nanoparticle. One or more discrete, continuous, differential, or integral NMR measurements are used to quantify one or more analyte(s) present in the sample solution containing the hydrogel coated magnetic nanoparticles, the one or more analyte(s) that reacts with one or more reactive binding moiety(ies) contained in the hydrogel.

The one or more reactive binding moiety(ies) of the responsive polymer transducers and methods of use described above may include one or more species of one or more binding moieties. For example, in one embodiment, the binding moieties may include one, two, or more types of oligonucleotides and/or one, two, or more types of proteins. Binding moieties may be a polymer, or may be part of a polymer that is linked to magnetic particle. The one or more reactive moiety(ies) may participate in a reaction resulting in a single product or participate in a reaction generating a cascade of reaction products. For example, a reactive moiety may be glucose oxidase, and in the presents of glucose, a reaction produces hydrogen peroxide and gluconic acid. The presence of hydrogen peroxide or gluconic acid changes the pH of the environment within the hydrogel or affect the extent of cross-linking of the hydrogel causing a reversible change in its permeability to solvent. In general one or more reactive moiety(ies) can react as to amplify the effect of changes in the physical or chemical properties of the hydrogel and subsequently changes in its permeability to solute and solvent within proximity of the magnetic nanoparticle and its magnetic field, magnetic field gradient when exposed to a magnetic field.

In still another aspect, the invention provides methods of determining the value of a physical parameter in a particular environment such as an analyte solution (e.g., a liquid sample). The method comprises the steps of exposing the transducer (nanoparticles with polymer matrix layer) of any of the types disclosed herein to the environment, and allowing a change in crosslink density of the matrix to occur in accordance with the environment (e.g., allowing equilibration of the matrix layer with the surrounding liquid sample, where the sample contains an analyte to which the matrix is responsive). Next, an external magnetic field is applied to the particle, and radio frequency pulse, preferably at or about the Larmor frequency, is applied to stimulate nuclei within the matrix adjacent the particle. Next, $T_1$ and/or $T_2$ relaxivity of the nuclei is detected, using, e.g., conventional magnetic relaxometer equipment or apparatus specially designed for the purpose, and the detected relaxivity signal is compared to a standard to determine the value of the parameter under investigation (e.g. via calibration curve(s) relating T1 and/or T2 relaxivity to the parameter under investigation, such as analyte presence or concentration in a liquid sample). The standard can take many specific forms, but may be generically described as a data set relating the relaxivity parameter to specific values for the parameter under study. It typically will be developed using physical or chemical stimuli or analytes having known specific parameter values and corresponding relaxivity readings. In some embodiments, e.g., where the researcher or technician or clinician seeks to determine the presence of some particular molecule, the standard may be merely a threshold value selected in the context of the performance goals intended for the system in use. In this regard, in a preferred embodiment the methods may be used to assess the presence and/or concentration of a molecule in an analyte solution, e.g., a biomolecule present in a biological fluid.

Provided responsive polymer matrix coated superparamagnetic nanosensors may be used for assessing the presence and/or concentration of one or more analyte in a biological fluid. The nanosensors are exposed to a biological fluid sample contained within a container (e.g., well) and the container (e.g., well) placed within a RF coil of an NMR detector. An RF excitation is applied to the container (e.g., well) at the appropriate wavelength, such wavelength being a calculable function of magnetic field strength and detected nuclei. The RF excitation produces one or more detectable RF signals, such as echoes, generated by the solvent (water) protons within magnetic field, magnetic field gradient of superparamagnetic nanoparticles, within the container (e.g., well), which is a function of the concentration or presence of the analyte in the fluid sample. The presence and/or concentration of the analyte of biological fluid sample can then be determined from the detected RF signal(s).

Provided responsive polymer matrix coated superparamagnetic nanosensors may be used as a transducer for sensing a physical or chemical stimulus. The transducer may comprise single responsive polymer matrix coated superparamagnetic nanosensor, as a group of nanosensors, an array of nanosensors, or in an encapsulation of nanosensors. The transducer operates in combination with an RF coil of an NMR detector. An RF excitation is applied to the transducer at the appropriate wavelength, such wavelength being a calculable function of magnetic field strength and detected nuclei. The RF excitation produces one or more detectable RF signals, such as echoes, generated by responsive polymer coated superparamagnetic nanosensors within the transducer. The physical or chemical stimulus can then be determined from the detected RF signal(s).

Provided responsive polymer matrix coated superparamagnetic nanosensors may be used for coating, e.g., in the form of a hydrogel membrane, one or more surface(s) of biosensors, medical devices, tools, instruments, and in vivo implants thus enabling smart or responsive devices. In particular embodiments, provided smart devices are used for the sensing of or within a biological cell, an organ, or biological fluids, or analytes within a biological cell, an organ, or biological fluids. In certain embodiments smart devices are used to sense the environment surrounding a device, a tool, an instrument, or an implant, or sense the physical properties and conditions of a device, a tool, an instrument, or an implant itself. The transducer coating operates in combination with an RF coil of an NMR detector. An RF excitation is applied to the transducer coating at the appropriate wavelength, such wavelength being a calculable function of magnetic field strength and detected nuclei. The RF excitation produces one or more detectable RF signals, such as echoes, generated by responsive polymer coated superparamagnetic nanosensors of the transducer coating or membrane. Further, in certain embodiments, one or more of the following: an atom, an ion, a molecule, a compound, a catalyst, an enzyme, an electroactive mediator, an electron-pair donor, an electron-pair acceptor, a lanthanide, an amino acid, a nucleic acid, an oligonucleotide, a therapeutic agent, a biological molecule, a metabolite of a therapeutic agent, a peptide, a polypeptide, a protein, a carbohydrate, a polysaccharide are loaded into one or more coated nanosensor(s) within the responsive hydrogel or the responsive hydrogel membrane itself and released in an opened loop or closed-loop controlled manner by a selective physical, chemical, or analyte stimulus applied to the responsive hydrogel membrane.

In FIG. 1, a principle on which the invention is based is explained on the basis of one embodiment, and serves not to limit the invention to a particular embodiment but for the purpose of explaining the principle. FIG. 1 shows device 100 which is a magnetic particle 101 coated with a responsive polymer matrix 102. Polymer matrix 102 is permeable to solvent molecule(s) 103. An example of solvent molecule 103 is water containing water protons. The responsive polymer matrix 102 contains cross-linked polymers.

FIG. 1a is a magnified cartoon representation of a small volume of responsive polymer matrix 102 in one state. Responsive polymer matrix 102 can have one or more binding moiety(ies). FIG. 1a depicts responsive polymer matrix 102 with binding moiety 105 cross-linked with binding moiety 106. Binding moiety 105 and 106 may be one or more polymer chains of the responsive polymer matrix 102 or atoms, ions, molecules, or compounds attached to a backbone of the responsive polymer matrix 102. Binding moiety 105 and binding moiety 106 are cross-linked through one or more covalent bonds, hydrogen bonds, van der Waals interactions, or physical entanglement of polymer chains represented by element 107. The extent of cross-linking through element 107 defines physical characteristics of a responsive polymer matrix 102, including porosity, swelling, de-swelling, volume fraction, and permeability. Responsive polymer matrix 102 can be a hydrogel. The extent of cross-linking of responsive polymer matrix 102 changes the specific volume fraction of device 100 leading to a change in diffusion time of solvent molecules 103 in the proximity of magnetic particle 101. Magnetic particle 101 is capable of dephasing spins of solvent molecule(s) 103, and dephasing is measurable using NMR detection of NMR relaxation rates (e.g., 1/T1, 1/T2). The specific volume change of device 100 and change in diffusion time of solvent molecule(s) 103 is proportional to the NMR relaxation rates (e.g., 1/T1, 1/T2) of a solvent molecule 103, with susceptibility-induced dephasing by magnetic nanoparticle 101. One or more discrete, continuous, differential, or integral NMR measurements can be used to quantify the magnitude or amount of stimulus 104.

In FIG. 1, a responsive polymer matrix 102 is configured with one or more binding moieties 105,106 as shown in FIG. 1a with sensitivity and specificity to a physical or chemical stimulus 104. Binding moieties 105,106 may include one or more species of one or more of the following: an atom, an ion, a molecule, a compound, an electroactive mediator, an electron-pair donor, an electron-pair acceptor. Binding moieties may be a polymer, or may be part of a polymer that is linked to magnetic particle. Binding moieties include functional groups, for example, binding moieties may include one or more species of one or more of the following: an amino group, a carboxyl group, a sulfhydryl group, an amine group, an imine group, an epoxy group, a hydroxyl group, a thiol group, an acrylate group, and/or an isocyano group. A physical or chemical stimulus 104 may be one or more physical or chemical stimuli include(s) thermal, mechanical, electromagnetic energy, electro-mechanical, electric field, electromotive force, magnetic field, magnetic force, magnetic gradient force, electromagnetic force, photoacoustic energy, photoacoustic forces, electromagnetic radiation, non-ionizing radiation, ionizing radiation, enzymatic reactions, catalytic reactions, acidic stimulus, and basic stimulus, pH change, changes in ionic strength, lipophilicity, hydrophobicity, and/or hydrophilicity.

When stimulus 104 is applied to device 100, the cross-linking of responsive polymer matrix 102 through one or more covalent bonds, hydrogen bonds, van der Waals interactions, or physical entanglement of the polymer chains represented by element 107 changes in a manner shown in FIG. 1b. FIG. 1b is a magnified depiction of responsive polymer 102 following transition into a responsive polymer matrix 109 upon receiving stimulus 104. Stimulus 104 causes element 107 to transition to element 108, whereby the interaction between binding moiety 105 and binding moiety 106 reduces the extent of cross-linking thus transforming polymer matrix 102 into responsive polymer 109. Responsive polymer 109 will be more permeable to solvent molecule(s) 103, thus enhancing the ability for solvent molecule(s) 103 to diffuse in and out of the responsive polymer 109 and similarly in and out of the magnetic field, the magnetic field gradient of magnetic particle 101. In some embodiments a responsive polymer of device 100 can be reversible upon cessation of the stimulus 104. In the absence of stimulus 104, binding moiety 105 can re-establish cross-linking with binding moiety 106, causing exclusion of solvent molecule(s) 103 from within the magnetic field, the magnetic field gradient of the magnetic particle 101, and subsequently from the responsive polymer matrix. Magnetic particle 101 is capable of dephasing spins of lesser proportion of solvent molecule(s) 103 within responsive polymer matrix 102 and the dephasing is measurable using NMR detection of NMR relaxation rates (1/T1, 1/T2). The magnitude or amount of stimulus 104 is proportional to NMR relaxation rates (1/T1, 1/T2) or delta T2 of NMR relaxation rates (e.g., of solvent molecules(s) 103). Thus, device 100 is a sensor or transducer for stimulus 104. The magnitude or amount of stimulus 104 can be quantified by proportion using one or more discrete, continuous, differential, or integral measurement(s) of NMR relaxation rates (e.g., 1/T1, 1/T2) of solvent molecules(s) 103 with an NMR detector. Device 100 can be calibrated for measurement of stimulus 104 by collecting a data set of NMR relaxation rates proportional to a predetermined range or standard of magnitude or amount of stimulus 104 and determining one or more calibration factors. One or more calibration factors will then be used to relate NMR relaxation rates to specific values for a stimulus 104.

FIG. 2 shows device 200 which is a responsive polymer membrane 202 containing magnetic particle(s) 201. Responsive polymer membrane 202 may be fabricated by combining one or more device 101 through self-assembly or fabrication methods that result in a sol-gel. A responsive polymer membrane 202 is permeable to solvent molecule(s) 203. An example of solvent molecule 203 is water containing water protons. Solvents highly susceptible to dephasing by magnetic particles may be use in lieu of water 203. A responsive polymer membrane 202 contains cross-linked polymers.

FIG. 2a is a magnified representation of responsive polymer membrane 202 in one state. Responsive polymer membrane 202 can have one or more binding moiety(ies). FIG. 2a shows a responsive polymer membrane 202 with binding moiety 205 cross-linked with binding moiety 206. Binding moiety 205 and 206 may be one or more polymer chains of a responsive polymer membrane 102 or atoms, ions, molecules, or compounds attached to a backbone polymer of a responsive polymer membrane 102. Binding moiety 205 and binding moiety 606 are cross-linked through one or more covalent bonds, hydrogen bonds, van der Waals interactions, or physical entanglement of a polymer chains represented by element 207. The extent of cross-linking through element 207 defines physical characteristics of a responsive polymer membrane 202 including porosity, swelling, de-swelling, volume fraction, and permeability. The extent of cross-linking of responsive polymer membrane 202 controls permeability of solvent molecule(s) 203 including its (their) amount and rate of translational diffusion in an out of a responsive polymer membrane 202 and within a proximity of magnetic particle(s) 201. Magnetic particle 201 is capable of dephasing spins of solvent molecule(s) 203 within responsive polymer membrane 202 and dephasing is measurable using NMR detection of NMR relaxation rates (1/T1, 1/T2). The flux or changes in flux of solvent molecule(s) 203, in and out of responsive membrane 202, subsequently in and out of a magnetic field, magnetic field gradient of the nanoparticle 201, is proportional to NMR relaxation rates (1/T1, 1/T2) of a solvent molecule 203 with susceptibility-induced dephasing by magnetic nanoparticle 201. One or more discrete, continuous, differential, or integral NMR measurements are used to quantify the magnitude or amount of stimulus 204.

In FIG. 2, a matrix takes the form of a responsive polymer membrane 202 is configured with one or more binding moieties 205,206 as shown in FIG. 2a with sensitivity and specificity to a physical or chemical stimulus 204. When stimulus 204 is applied to device 200, the cross-linking of responsive polymer membrane 202 through one or more covalent bonds, hydrogen bonds, van der Waals interactions, or physical entanglement of polymer chains represented by element 207 are changed in a manner shown in FIG. 2b. FIG. 2b is a magnified representation of responsive polymer membrane 209 which has transitioned from responsive polymer membrane 202 of FIG. 2a upon receiving stimulus 204. Stimulus 204 causes element 207 to transition to element 208 whereby an interaction between binding moiety 205 and binding moiety 206 reduces the extent of cross-linking thus transforming polymer membrane 202 of FIG. 2a into responsive polymer membrane 209. Responsive polymer 209 is more permeable to solvent molecule(s) 203 thus enhancing the ability for solvent molecule(s) 203 to diffuse in and out of responsive polymer 209 and similarly in and out of magnetic field(s), magnetic field gradient(s) of magnetic particle(s) 201. The characteristics of responsive polymer membrane 202 of device 200 are reversible upon cessation of a stimulus 204. In the absence of stimulus 204, binding moiety 205 may re-establish cross-linking with binding moiety 206 causing exclusion of solvent molecule(s) 203 from within a magnetic field(s), a magnetic field gradient(s) of a magnetic particle(s) 201 and subsequently from a responsive polymer membrane. Magnetic particle(s) 201 is (are) capable of dephasing spins of lesser proportion of solvent molecule(s) 203 within responsive polymer membrane 209 and dephasing is measurable using NMR detection of NMR relaxation rates (e.g., 1/T1, 1/T2). The magnitude or amount of stimulus 204 is proportional to NMR relaxation rates (1/T1, 1/T2) or delta of NMR relaxation rates of solvent molecules(s) 203. Thus device 201 is a sensor or transducer for stimulus 204 and may also be used as a flux sensor or flux transducer of solute, or solvent, or solution, or combination thereof. The magnitude, or amount, or rate of change of a stimulus 204 is quantified by proportion using one or more discrete, continuous, differential, or integral measurements of NMR relaxation rates (e.g., 1/T1, 1/T2) with an NMR detector. Similarly, the magnitude, or amount, or rate of change of amount of solvent(s) 203 flowing through responsive membrane 201 is quantified by proportion using one or more discrete, continuous, differential, or integral measurements of NMR relaxation rates (e.g., 1/T1, 1/T2) with an NMR detector. Device 200 may be calibrated for measurement of stimulus 204 by collecting a data set of NMR relaxation rates proportional to a predetermined range or standard of magnitude or amount of stimulus 204 and determining one or more calibration factors. One or more calibration factors are then used to relate NMR relaxation rates to specific values for a stimulus 204. Similarly, device 200 may be calibrated for measurement of magnitude, or amount, or rate of change of an amount of solvent(s) 203 flowing through responsive membrane 201 by collecting a data set of NMR relaxation rates proportional to a predetermined range or standard of magnitude, or amount, or rate of change of an amount of solvent(s) 203 flowing through responsive membrane 201 and determining one or more calibration factors. One or more calibration factors are then used to relate NMR relaxation rates to specific values for magnitude, or amount, or rate of change of an amount of solvent(s) 203 flowing through responsive membrane 201.

FIG. 3 shows device 300 which is a magnetic particle 301 coated with a responsive polymer matrix 302. A polymer matrix 302 is permeable to solvent molecule(s) 303. An example of solvent molecule 303 is water. Responsive polymer matrix 302 contains cross-linked polymers.

FIG. 3a is a magnified representation of responsive polymer matrix 302 in one state. Responsive polymer matrix 302 can have one or more binding moiety(ies). FIG. 3a shows a responsive polymer matrix 302 with binding moiety 305. Binding moiety 305 may be, e.g., an antibody or antigen attached to one or more polymer(s) of a responsive polymer matrix 302. Binding moiety 305 may also be, e.g., a nucleic acid polymer chain bound to one or more polymer chains of a responsive polymer matrix 302. Binding moiety 305 is attached to responsive matrix 302 through one or more covalent bonds, hydrogen bonds, van der Waals interactions, or physical entanglement with polymer chains. Responsive polymer 302 can be a hydrogel. The extent of cross-linking of responsive polymer matrix 302 will change a specific volume fraction of device 300 leading to a change in diffusion time of solvent molecules 303 in proximity of magnetic particle 301. Magnetic particle 301 is capable of dephasing spins of solvent molecule(s) 303 and dephasing is measurable using NMR detection of NMR relaxation rates (1/T1, 1/T2). A specific volume change of device 300 and a change in diffusion time of solvent molecule(s) 303 is proportional to NMR relaxation rates (e.g., 1/T1, 1/T2) of a solvent molecule 303 with susceptibility-induced dephasing by magnetic nanoparticle 301. One or more discrete, continuous, differential, or integral NMR measurements are used to quantify magnitude or amount of antigen or antibody within a solution or biological fluid sample.

In FIG. 3, in one embodiment, a responsive polymer matrix 302 is configured with a binding moiety 305 as shown in FIG. 3a with sensitivity and specificity to an antigen 304. When a solution containing the presence of antigen 304 is applied to device 300, cross-linking of responsive polymer matrix 302 through one or more covalent bonds, hydrogen bonds, van der Waals interactions, or physical entanglement of polymer chains changes in a manner shown in FIG. 3b. FIG. 3b is a magnified representation of responsive polymer 302 of FIG. 3a which has transitioned into responsive polymer matrix 306 upon inclusion of antigen 304. Antigen 304 causes responsive polymer matrix 306 to increase the extent of cross-linking thus transforming polymer matrix 302 into responsive polymer 306. Responsive polymer 306 is less permeable to solvent molecule(s) 303 thus reducing the ability for solvent molecule(s) 303 to diffuse in and out of responsive polymer 306 and similarly in and out of a magnetic field, a magnetic field gradient of magnetic particle 301. A responsive polymer of device 300 can be reversible upon displacement of antigen 304. Displacement of antigen 304 may take place by physical or chemical stimuli. In the absence of antigen 304, responsive polymer 306 may transition back to responsive polymer 302 enhancing flux of solvent molecule(s) 303 into a responsive polymer matrix and, subsequently, within a magnetic field, a magnetic field gradient of magnetic particle 301. Magnetic particle 301 is capable of dephasing spins of higher proportion of solvent molecule(s) 303 within responsive polymer matrix 306 and dephasing is measurable using NMR detection of NMR relaxation rates (e.g., 1/T1, 1/T2). The amount or concentration of antigen 304 is proportional to NMR relaxation rates (e.g., 1/T1, 1/T2) or delta of NMR relaxation rates (e.g., $\Delta 1/T1$, $\Delta 1/T2$) of solvent molecules(s) 303. Thus device 301 is a sensor or transducer for antigen 304. The amount, concentration, or rate of change of concentration of antigen 304 is quantified by proportion using one or more discrete, continuous, differential, or integral measurements of NMR relaxation rates (e.g., 1/T1, 1/T2) with an NMR detector. Device 300 may be calibrated for measurement of antigen 304 by collecting a data set of NMR relaxation rates proportional to a predetermined range or standard of magnitude, amount, or concentration of antigen 404 and determining one or more calibration factors. One or more calibration factors can then be used to relate NMR relaxation rates to specific values for magnitude, amount, or concentration of antigen 404.

FIG. 4 shows device 400 which is a magnetic particle 401 coated with a responsive polymer matrix 402. A polymer matrix 402 is permeable to solvent molecule(s) 403. An example of solvent molecule 403 is water containing water protons. A responsive polymer matrix 402 contains cross-linked polymers.

FIG. 4a is a magnified representation of responsive polymer matrix 402 in one state. Responsive polymer matrix 402 can have one or more binding moiety(ies). FIG. 4a shows a responsive polymer matrix 402 with binding moiety 405 cross-linked with binding moiety 406. Binding moiety 405 and binding 406 is antibody-antigen complex with each moiety bound to one or more polymer chains of responsive polymer matrix 402. Binding moiety 405 and binding moiety 406 enhances cross-linking of responsive polymer matrix 402 through their complexation. The extent of cross-linking by binding moiety 405 and binding moiety 405 defines the physical characteristics of responsive polymer matrix 402 including porosity, swelling, de-swelling, volume fraction, and permeability. Responsive polymer 402 can be a hydrogel. The extent of cross-linking of responsive polymer matrix 402 changes the specific volume fraction of device 400 leading to a change in diffusion time of solvent molecules 403 in the proximity of magnetic particle 401. Magnetic particle 401 is capable of dephasing spins of solvent molecule(s) 403 and dephasing is measurable using NMR detection of NMR relaxation rates (e.g., 1/T1, 1/T2). The specific volume change of device 100 and change in diffusion time of solvent molecule(s) 403 is proportional to NMR relaxation rates (e.g., 1/T1, 1/T2) of a solvent molecule 403 with susceptibility-induced dephasing by magnetic nanoparticle 401. One or more discrete, continuous, differential, or integral NMR measurements are used to quantify amount, concentration, or rate of change of concentration of antigen, antibody, or nucleic acid polymer 404.

In FIG. 4, for one embodiment, a responsive polymer matrix 402 is configured with antibody-antigen complex binding moieties 405,406 as shown in FIG. 4a with sensitivity and specificity to each other. When free antigen 404 is applied to device 400, the cross-linking of responsive polymer matrix 402 through antibody-antigen complex of binding moieties 105,106 are changed in a manner shown in FIG. 4b. FIG. 4b is a magnified representation of responsive polymer 402 which has transitioned into responsive polymer matrix 409 with the presence of free antigen 404. Free antigen 404 competes with one bound moiety of an antibody-antigen complex 405,406 and reduces the extent of cross-linking of a responsive polymer matrix 402 between an antibody-antigen complex 405,406 thus transforming polymer matrix 402 into responsive polymer 409. Responsive polymer 409 is more permeable to solvent molecule(s) 403 thus enhancing the ability for solvent molecule(s) 403 to diffuse in and out of responsive polymer 409 and similarly in and out of a magnetic field, a magnetic field gradient of magnetic particle 401. Responsive polymer of device 400 can be reversible upon the absence of free antigen 404. In the absence of free antigen 404, binding moiety 405 may re-establish binding with binding moiety 406 causing exclusion of solvent molecule(s) 403 from within a magnetic field, a magnetic field gradient of the magnetic particle 401 and subsequently from responsive polymer matrix 409. Magnetic particle 401 is capable of dephasing spins of lesser proportion of solvent molecule(s) 403 within responsive polymer matrix 409 and dephasing is measurable using NMR detection of NMR relaxation rates (e.g., $1/T1$, $1/T2$). The magnitude or amount of stimulus 404 is proportional to the NMR relaxation rates (e.g., $1/T1$, $1/T2$) or delta of NMR relaxation rates (e.g., $\Delta 1/T1$, $\Delta 1/T2$) of solvent molecules(s) 403. Thus device 400 is a sensor or transducer for free antigen 404. The amount, concentration, or rate of change of concentration of free antigen 404 can be quantified by proportion using one or more discrete, continuous, differential, or integral measurement(s) of NMR relaxation rates (e.g., $1/T1$, $1/T2$) of solvent molecules(s) 403 with an NMR detector. Device 400 may be calibrated for measurement of free antigen 404 by collecting a data set of NMR relaxation rates proportional to a predetermined range or standard of magnitude, amount, or concentration of free antigen 404 and determining one or more calibration factors. One or more calibration factors can then be used to relate NMR relaxation rates to specific values for magnitude, amount, and/or concentration of free antigen 404.

FIG. 5 shows device 500 which is a magnetic particle 501 coated with a responsive polymer matrix 502. A polymer matrix 502 is permeable to solvent molecule(s) 103. An example of solvent molecule 503 is water containing water protons. Responsive polymer matrix 502 contains cross-linked polymers.

FIG. 5a is a magnified representation of responsive polymer matrix 502 in one state. Responsive polymer matrix 502 can have one or more binding moiety(ies). FIG. 5a shows responsive polymer matrix 502 with one or more binding moiety(s) 505 cross-linked with binding moiety 106 having one or more binding sites with affinity for binding moiety 505. Binding moiety 505 and binding moiety 506 are cross-linked through one or more hydrogen bonds, van der Waals interactions, or physical entanglement. The extent of cross-linking between one or more binding moiety 505 and binding moiety 506 defines physical characteristics of a responsive polymer matrix 502 including porosity, swelling, de-swelling, volume fraction, and permeability. Responsive polymer 502 can be a hydrogel. The extent of cross-linking of responsive polymer matrix 502 changes the specific volume fraction of device 500 leading to a change in diffusion time of solvent molecules 503 in the proximity of magnetic particle 501. Magnetic particle 501 is capable of dephasing spins of solvent molecule(s) 503 and dephasing is measurable using NMR detection of NMR relaxation rates (e.g., $1/T1$, $1/T2$). The specific volume change of device 500 and the change in diffusion time of solvent molecule(s) 503 is proportional to NMR relaxation rates (e.g., $1/T1$, $1/T2$) of a solvent molecule 503 with susceptibility-induced dephasing by magnetic nanoparticle 501. One or more discrete, continuous, differential, or integral NMR measurements are used to quantify amount, concentration, or rate of change of concentration of analyte 504.

In FIG. 5, a responsive polymer matrix 502 is configured with one or more binding moieties 505,506 as shown in FIG. 5a with sensitivity and specificity to an analyte 504. In one embodiment, analyte 504 has similar or equivalent reactive group(s) to binding moiety 505 so an analyte 504 of interest or its equivalent is attached to responsive polymer matrix 502 in advance. When free analyte 504 is applied to device 500, the cross-linking of responsive polymer matrix 502 is changed in a manner shown in FIG. 5b. FIG. 5b is a magnified representation of responsive polymer 502 which has transitioned into responsive polymer matrix 509 in the presence of free analyte 504. Free analyte 504 competes with one or more bound moiety(ies) of complex 505,506 and displaces bound moiety 506 from cross-linking with responsive polymer matrix 502, thus transforming polymer matrix 502 into responsive polymer matrix 509. Responsive polymer 509 is more permeable to solvent molecule(s) 503, thus enhancing the ability for solvent molecule(s) 503 to diffuse in and out of responsive polymer 509 and similarly in and out of a magnetic field, a magnetic field gradient of a magnetic particle 501. A responsive polymer of device 500 can be reversible in the absence of analyte 504. In the absence of analyte 504, binding moiety 505 may re-establish cross-linking with binding moiety 506 causing exclusion of solvent molecule(s) 503 from within a magnetic field, a magnetic field gradient of a magnetic particle 501 and subsequently from responsive polymer matrix 509. Magnetic particle 501 is capable of dephasing spins of lesser proportion of solvent molecule(s) 503 within responsive polymer matrix 509 and dephasing is measurable using NMR detection of NMR relaxation rates (e.g., $1/T1$, $1/T2$). The magnitude or amount of stimulus 504 is proportional to the NMR relaxation rates (e.g., $1/T1$, $1/T2$) or delta of NMR relaxation rates (e.g., $\Delta 1/T1$, $\Delta 1/T2$) of solvent molecules(s) 503. Thus device 500 is a sensor or transducer for analyte 504. The amount, concentration, or rate of change of concentration of analyte 504 can be quantified by proportion using one or more discrete, continuous, differential, or integral measurement(s) of the NMR relaxation rates (e.g., $1/T1$, $1/T2$) of solvent molecules(s) 503 with an NMR detector. Device 500 may be calibrated for measurement of free analyte 504 by collecting a data set of NMR relaxation rates proportional to a predetermined range or standard of magnitude, amount, or concentration of free analyte 504 and determining one or more calibration factors. One or more calibration factors are then used to relate NMR relaxation rates to specific values for magnitude, amount, or concentration of free analyte 504.

In one embodiment, devices 100 of FIG. 1 are prepared using a surfactant-free emulsion polymerization (SFEP) to encapsulate each iron oxide particle of approximately 10 nm in diameter within a large spherical responsive polymer matrix 102. This will produce a stable, compact and chemically stable polymer overlay. Before emulsion polymerization, surfaces of each iron oxide particle may be modified by adsorption of oleic acid. In one method, a jacketed cylindrical reaction vessel was changed with 180 mL of water and 20 mL of the iron oxide dispersion. After 30 minutes of deoxygenating, 30 mL of styrene (St. Aldrich), 3 mL of methyl methacrylate (MMA, Aldrich), and 0.2 g sodium styrene sulfonate (NaSS, Polyscience) were added into the vessel. The temperature was increased to 70° C. and 2.0 g ammonium persulfate (APS, Aldrich) was added to initiate polymerization, which reacted for 5 hours. In another method, after adsorption of oleic acid, an approximately 94:6 wt % ratio of poly (N-isopropylacrylamide)-NIPAM (26.1 mL, 0.01 M): acrylic acid-Aac(1.6 mL, 0.01 M) is then added and stirred. The solution is heated to 71° C. in an oil bath, and then APS (0.8 mL, 0.01 M) added to initiate the polymerization. The reaction time, which depends on the amount of starting materials, is varied between 6 and 8 hours. At the end of this period, the solution is cooled and filtered through a 1 micron membrane to remove any micrometer size impurities and or any aggregate particles. The filtered solution may be centrifuged at 20° C. for 2 hours at 3500 rpm and the supernatant separated to remove unreacted materials, soluble side products, and seeds of pure polymer. The purified nanoparticles are than diluted with pure water and stored at room temperature. The size of the hydrogel coated nanoparticles can be varied between 100-230 nm by controlling the amount of monomer and initiator as well as reaction time. Specific binding moieties may be attached to the hydrogel with using known covalent conjugation and or physical adsorption methods.

Figure 6:
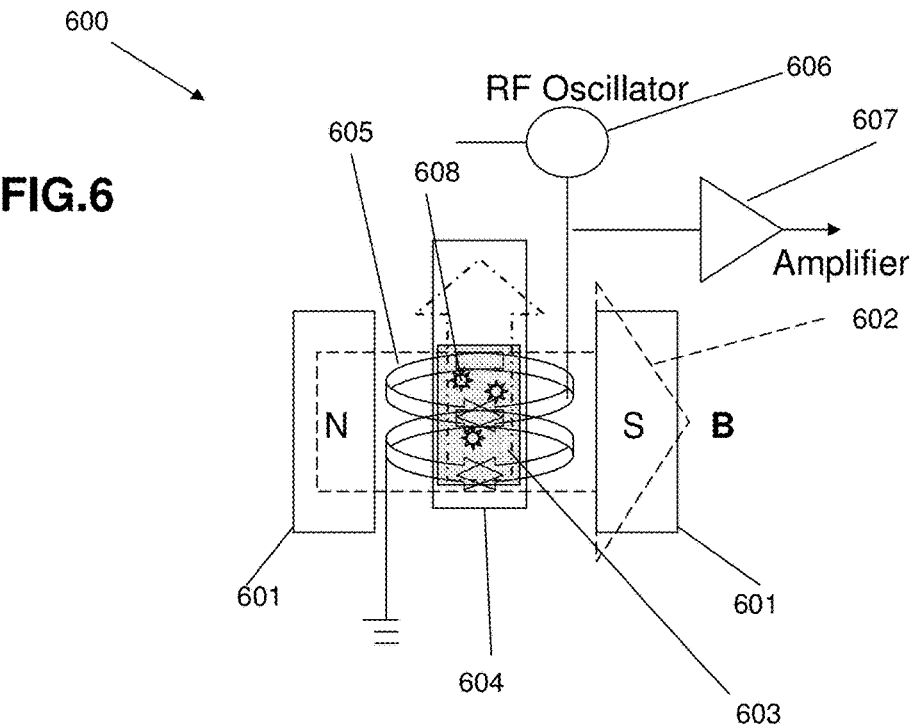
FIG. 6 is a schematic that depicts a principle of operation and device elements for performing NMR measurements using responsive polymer matrix coated nanosensors, and/or bioanalytical assays for analyte detection according to illustrative embodiments of the invention.

FIG. 6 is a schematic diagram 600 of an NMR system for detection of an echo response of a sample 603 to an RF excitation, thereby detecting the presence and/or concentration of an analyte in a sample. In a specific embodiment, bias magnets 601 establish a bias magnetic field Bb 602 through a sample 603. In alternative embodiments, other configurations of bias magnetic field Bb 602 can be applied to sample container 604 including, unilateral magnetic fields, low powered magnetic fields, and the earth's magnetic field. Reagents (e.g., including, e.g., provided nanosensors) 608 are added in sample container 604 prior or introduced simultaneously with sample 603 into container 604. An RF coil 605 and RF oscillator 606 provides an RF excitation at the Larmor frequency which is a linear function of the bias magnetic field Bb. In one embodiment, RF coil 605 is wrapped around sample container 604. In alternative embodiments, RF coil 605 can be a planar RF coil or other shape and form of RF coil can be used with sample container 604. The excitation RF creates instability in the spin of water protons (or free protons in a non-aqueous solvent) within responsive hydrogel matrices of nanosensors. When the RF excitation is turned off, protons "relax" to their original state and emit an RF signal characteristic of the concentration of analyte. Coil 605 acts as an RF antenna and detects an "echo" of the relaxation. The echoes of interest are decay in time T1 and/or T2. The RF signal from coil 605 is amplified by amplifier 607 and processed to determine a change in decay time (e.g., T1, T2) in response to excitation in the bias field Bb 602. Various configurations of container 604 (e.g., well, channel, reservoir, etc.) may be used for analyte detection.

Figure 7:
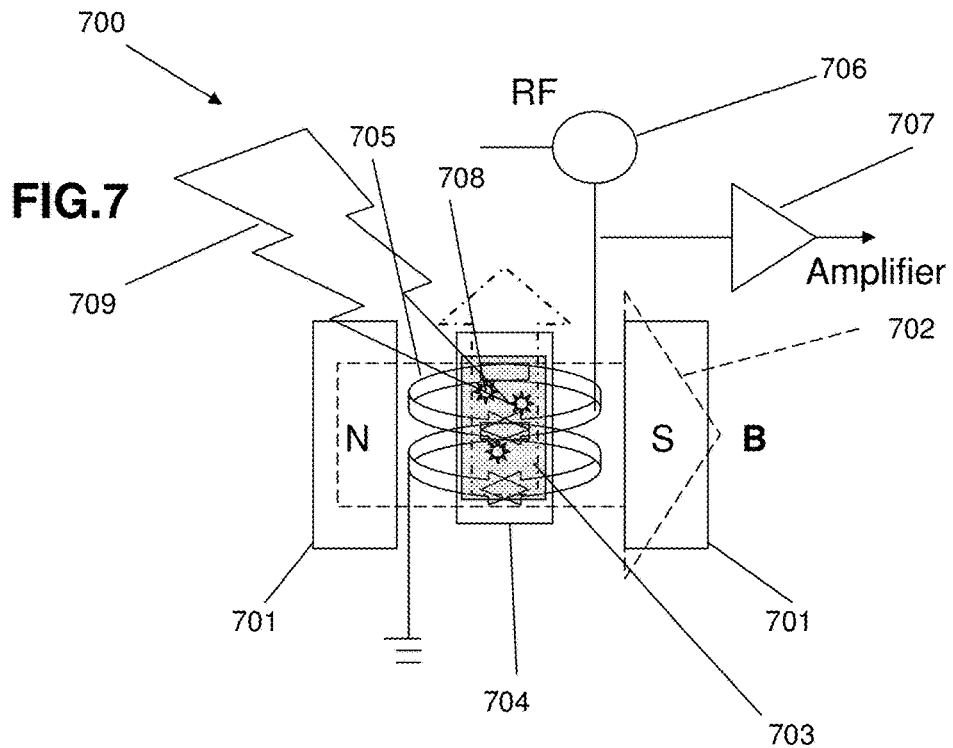
FIG. 7 is a schematic that demonstrates the principle of operation and device elements for performing NMR measurements of responsive polymer matrix coated nanosensors for detection of a stimulus, according to an illustrative embodiment of the invention.

FIG. 7 is a schematic diagram 700 of an NMR system for detection of an echo response of a solution 703 to an RF excitation, thereby detecting a physical or chemical stimulus 709 applied to solution 703 containing the nanosensors 708 (e.g., provided nanosensors). In a specific embodiment, bias magnets 701 establish a bias magnetic field Bb 702 through solution 703. In alternative embodiments, other configurations of bias magnetic field Bb 702 can be applied to structure 704 including, unilateral magnetic fields, low powered magnetic fields, and the earth's magnetic field. Provided nanosensors 708 are contained within structure 704. Structure 704 may be an open or sealed container including but limited to a well, a glass capillary, a glass cell, or any structure for confining a volume of solution containing one or more nanosensors 708. Structure 704 can be made of any material that can amplify, enhance, or retard, in a controlled manner, the magnitude of the physical or chemical stimulus applied to solution 703. Structure 704 may be permeable to a physical or chemical stimulus applied to solution 703. Various transducers, conductors, resistors, can be applied to one or more surface(s) or incorporated within one or more surface(s) of structure 704 including electrodes, piezoelectric materials, and thermocouples. An RF coil 705 and RF oscillator 706 provides an RF excitation at the Larmor frequency which is a linear function of the bias magnetic field Bb 702. In one embodiment, RF coil 705 is wrapped around structure 704. In alternative embodiments, RF coil 705 can be a planar RF coil or other RF coil shape and form of can be used with structure 704. The excitation RF creates instability in the spin of water protons (or free protons in a non-aqueous solvent) within responsive hydrogel matrices of nanosensors 708. When the RF excitation is turned off, protons "relax" to their original state and emit an RF signal characteristic of a physical or chemical stimulus applied to solution 703. Coil 705 acts as an RF antenna and detects an "echo" of the relaxation. The echoes of interest are decay in time (e.g., T1 and/or T2). The RF signal from the coil 705 is amplified 707 and processed to determine a change in decay time (e.g., T1, T2) in response to excitation in the bias field Bb 702. Sample solution 703 may be replaceable with a hydrogel or a membrane containing one or more nanosensors 708.

Figure 8:
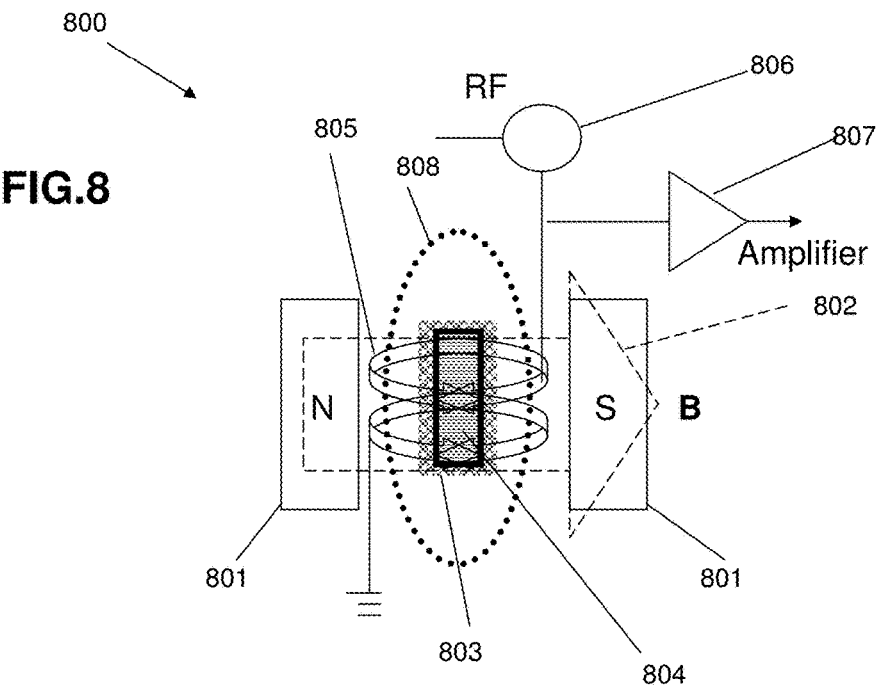
FIG. 8 is a schematic of an NMR system for detection of an echo response of a layer containing one or more provided nanosensors attached or coated onto one or more wall(s) of a device implant.

FIG. 8 is a schematic diagram 800 of an NMR system for detection of an echo response of a layer 803 containing one or more nanosensors (e.g., provided nanosensors) attached or preferably coated onto one or more wall of device implant 804. Layer 803 can contain discrete nanosensors attached by nonspecific absorption or specific chemical coupling to at least one surface of device implant 804. Nanosensors may be partially coated with a responsive coating whereby the coated portion of nanosensors excludes portions of nanoparticles attached to a surface of device implant 804. Device implant 804 may be placed into one or more biologic cell, organ, or whole body 808. In a specific embodiment, bias magnets 801 establish a bias magnetic field Bb 802 to layer 803 of device implant 804 within body 808. In alternative embodiments, other configurations of bias magnetic field Bb 802 can be applied to a biologic body 808 including, unilateral magnetic fields, low powered magnetic fields, and the earth's magnetic field. An RF coil 805 and RF oscillator 806 provides an RF excitation at the Larmor frequency which is a linear function of the bias magnetic field Bb 802. In one embodiment, RF coil 805 is wrapped around body 808. In alternative embodiments, RF coil 805 can be a planar RF coil or other RF coil shape and form of can be used to apply an RF excitation to body 808 and subsequently to layer 803. The excitation RF creates instability in the spin of water protons (or free protons in a non-aqueous solvent) within responsive hydrogel matrices of nanosensors of layer 803. When the RF excitation is turned off, the protons "relax" to their original state and emit an RF signal characteristic of the physical parameters sensed by layer 803. Coil 805 acts as an RF antenna and detects an "echo" of the relaxation. The echoes of interest are the decay in time (e.g., T1 and T2). The RF signal from coil 805 is amplified 807 and processed to determine a change in decay time (e.g., ΔT1, ΔT2) in response to the excitation in the bias field Bb 802. In an alternative embodiment, device implant 804 coated with layer 803 can be monitored using an NMR imager.

Figure 9:
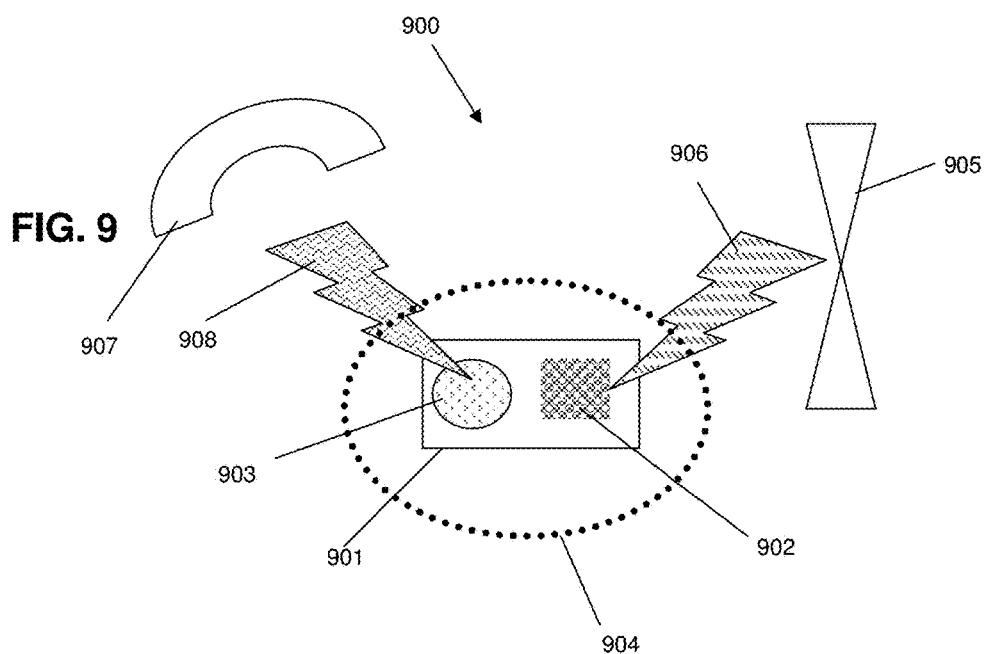
FIG. 9 is a schematic depicting a principle of operation and device elements of a smart device for sensing and control release of one or more binding moieties.

FIG. 9 is a cartoon schematic of a principle of operation and elements of a smart device 900. Smart device 900 comprises a matrix 901 having a sensing element 902 and a control release element 903. Smart device 900 can be placed within, inserted into, or implanted inside a biologic, cell, organ, or body 904. Sensing element 902 can be one or more provided transducers. Sensing element 902 may emit one or more RF echo signal 906 generated using the NMR principle and methods of detection as described herein. One or more RF echo signal 906 may be detected by a RF antenna 905 of an NMR detector. Sensing element 902 provides measurements of one or more physical, chemical or analyte stimuli within an environment and in the vicinity of smart device 900. Measurement results from sensing 902 can be used to control a physical or chemical stimulus emitter 907. Stimulus emitter 907 can be used to apply a stimulus 908 to control release element 903. Reception of stimulus 908 by control release element 903 allows one or more of the following binding moieties: an atom, an ion, a molecule, a compound, a catalyst, an enzyme, an electroactive mediator, an electron-pair donor, an electron-pair acceptor, a lanthanide, an amino acid, a nucleic acid, an oligonucleotide, a therapeutic agent, a biological molecule, a metabolite of a therapeutic agent, a peptide, a polypeptide, a protein, a carbohydrate, a polysaccharide to be released or delivered out of matrix 901 and into a biologic, cell, organ, or body 904. Smart device 900 can be configured to operate in an open loop, as previously described, or closed-loop control manner. In a closed-loop manner, smart device 900 may comprise a sensing element 902, a miniaturized NMR detector functioning in conjunction with sensing element 902, a control release element 903, a stimulus emitter 907, microelectronics for implementing a close-loop control system, and a power source. As an example, element 902 can detect glucose and control release element 903 is capable of releasing insulin. Element 902 can glucose concentration within body 904 and will release insulin in a controlled manner as to allow body 904 to establish or maintain a normal glucose concentration. Smart device 900 will thus function as an artificial pancreas.

Provided NMR detection systems can measure either a positive or negative change in relaxation rates (e.g., ΔT1 and ΔT2). In one embodiment, provided systems and methods measure T2 changes due to a stimulus or an analyte binding event, leading to positive and negative T1 or T2 changes. In one aspect, an NMR detection system will measure baseline T2 of a solution containing a responsive polymer coated nanoparticles first, and then will be mixed with liquid sample containing an analyte, and T2 will be measured again to determine whether a change in T2 has occurred in the presence of analyte. A quality control step can be performed to minimize errors that may affect the measurement of analyte including stoichiometry, metering, mixing, variations in nanoparticle properties, and fluidic transport.

In one embodiment provided compositions and methods can be used to detect analyte by measuring NMR echo signals from a sample at a single time. Alternatively, an NMR detection system can perform a series of measurements spanning a period of time and/or may compare or analyze measurements to improve detection of analyte. For example, binding between analyte and nanosensors may proceed during an interval which is longer than the time required for a particular measurement. An NMR system may perform measurements repeatedly to observe changes caused by binding. Repeated measurements can greatly enhance accuracy of results by reducing false negatives and/or false positives, providing a lower detection threshold, and enhancing the detection probability for a given stimulus or quantity of an analyte. An NMR detection system can also derive parameters related to reaction kinetics from repeated measurements on a same sample, including a rate of change of a parameter or an accumulated reaction parameter. A multiple scanning protocol combined with a rate-magnitude analysis can enhance both reliability and threshold sensitivity of a detection system.

A model suggests a positive T2 change is due to reactions whereby water molecules are displaced further from a responsive polymer coated nanoparticles upon an occurrence of a stimulus or analyte binding event. A negative T2 change is due to repeated dephasing of more water molecules diffusing in closer proximity to nanoparticles upon a stimulus or analyte binding event. A simplified nanoparticle is assumed to consist of a spherical core of superparamagnetic material, surrounded by a spherical shell of hydrogel, all in water. However, the model can be applied or modified for use with nanoparticles of other shapes and for use with other solvents. Without being bound by theory, the model suggests the following mechanisms for observed T2 changes:

(1) Nanoparticles in solution reduce T2 relative to plain water. The model suggests that depolarization is due to a dipole magnetic field produced by a magnetized core. Field distortion causes spins to precess at different frequencies, leading to destructive interference. Although CPMG normally refocuses static field-nonuniformity effects, Brownian motion of water molecules causes them to enter and exit field distortions in a time shorter than the echo interval, thereby making the spin dispersion time-dependent and breaking the CPMG refocusing effect.

(2) Water flux in the proximity of nanoparticles result in delta changes of T2. Delta changes in T2 are directly proportional to specific volume fraction of responsive polymer coated nanoparticles and diffusion of water in the proximity of the nanoparticles. Water flux within the spherical shell are due to analyte molecules modifying permeability of a spherical shell surrounding nanoparticles and regions around a nanoparticle, thereby enhancing or decreasing water fluxes from that region, changing the specific volume fraction of the spherical shell. A change in specific volume fraction effects the diffusion interaction between nanoparticles and water molecules thus enhancing or reducing spin dispersion, and increasing or decreasing T2. A single exponential usually fits the polarization decay curve of T2. In the case of a T2 decrease, hydrogens close to nanoparticles are strongly dephased, while a general solvent sees only a uniform field, a two-population system. However, spin populations are rapidly equilibrated across a sample by spin diffusion via homonuclear flip-flop interactions, resulting in a single averaged T2.

Provided NMR detection systems may detect a stimulus or presence of an analyte by analyzing the magnetic resonance signals by spectral analysis to seek a frequency component characteristic of the occurrence of a stimulus or analyte binding event. Alternatively the step could include applying a CPMG procedure, and analyzing signals to determine T1 and/or T2 of a solution. The T1 or T2 distribution may be a single exponential component, or it may include a multitude of components, depending on spin diffusion rate. A delta T1 or delta T2 from a baseline measurement of nanosensors without a stimulus or analyte and indicates the occurrence of a stimulus or presence of an analyte.

Provided NMR detection measurement methods may include the steps of measuring T1 or T2 value of a standard. Here a standard is any material which has a known T1 or T2. Preferably the T1 or T2 of the standard is unchanging in time and is known from prior calibration measurements. For example a standard may be a solution of nanosensors with a concentration adjusted to provide a particular value of T1 or T2. Standards enable detection and correction of instrumentation drifts. A standard may be a solution or encapsulation of nanosensors selected to have a T1 or T2 in a desired range. A standard may be arranged to have a T1 or T2 substantially equal to that of a stimulus-free or an analyte-free sample; an analytical negative control. The standard may have a T1 or T2 close to that produced by a stimulus or analyte; a analytical positive control. The method may include measuring T1 or T2 of multiple standards with different T1 and T2 values.

In an illustrative, constructive embodiment, device 100 of FIG. 1 is designed as a temperature nanosensor. Binding moieties 105,106 comprises hydrophobic groups such as methyl, ethyl and propyl groups. For example, responsive polymer matrix 102,109 is poly (N-isopropylacrylamide) (PNIPAAm). PNIPAAm has a low critical solution temperature (LCST) in the range of 25-32° C. PNIPAAm decreases their water-solubility as temperature increases and shrink as temperature increases above the LCST. At low temperatures, hydrogen bonding between hydrophilic segments of binding moieties 105,106 and water dominates, leading to enhanced dissolution of water. As temperature increases, hydrophobic interactions among hydrophobic segments of binding moieties 105,106 become strengthened, while hydrogen bonding becomes weaker. The net result is shrinking of responsive matrix 102,109 due to inter-polymer chain association through hydrophobic interactions resulting in flux of water of out of responsive matrix 102,109. A decrease in specific volume fraction of matrix 102 will result in a decreased NMR relaxation rate (e.g., 1/T1, 1/T2). In this design, temperature is inversely proportional to NMR relaxation rates.

In an illustrative, constructive embodiment, device 200 of FIG. 2 is designed as an electro-sensitive hydrogel membrane. Binding moieties 205, 206 of one or more nanosensors within a hydrogel membrane or a membrane is made of sodium acrylic acid-acrylamide copolymer. Membrane device 200 contains an aqueous solution (e.g., acetone and water). Membrane device 200 is placed between two planar electrodes. The planar electrodes are used to apply and electric field to a solution containing membrane device 200. In the absence of electrolytes or in the presence of low concentration of electrolytes, application of an electric field will cause the membrane and/or one or more nanosensors to shrink. For example, due to a migration of sodium ion $Na^+$ to a cathode electrode will result in changes in carboxyl groups of polymer chains one or more binding moiety 205, 206 from —$COO^-Na^+$ to —COOH. In the presence of high concentration of electrolytes in solution, however, more $Na^+$ enters the membrane and the membrane swells. Shrinking and swelling due to the applied electric field decreases and increases specific volume fraction of the membrane resulting in decreases and increases of NMR relaxation rates (e.g., 1/T1, 1/T2). NMR echo signals may be used to detect electrolyte concentration and/or their migration in a solution.

In an illustrative, constructive embodiment, device 100 of FIG. 1 is designed as a glucose nanosensor. Responsive matrix 102 is made of a block co-polymer of N, N dimethylaminoethyl methacrylate (DEA) and 2-hydroxypropyl methacrylate (HPMA) with cross-linking binding moieties 105,106 comprising glucose oxidase immobilized by polyacrylamide polymer chains. In the presence of glucose, glucose oxidase converts glucose to produce gluconic acid which changes the pH of the environment within responsive matrix 102. Responsive matrix 102 swells as a result from the ionization of the amine groups by the lowering pH. An increase in specific volume fraction of responsive matrix 102 results in a decrease the NMR relaxation rates (e.g., 1/T1, 1/T2). In this design, glucose concentration is inversely proportional to NMR relaxation rates.

In an illustrative, constructive embodiment, device 400 of FIG. 4 is designed as an analyte specific nanosensor. An antigen-antibody complex using binding moieties 405, 406 is incorporated into responsive matrix 402. For example, rabbit immunoglobulin G (IgG), the antigen, is chemically modified by coupling it with N-succinimidylacrylate (NSA) in phosphate buffer solution to introduce vinyl groups into the rabbit IgG. Resultant vinyl rabbit IgG is then mixed with antibody, goat rabbit IgG (GAR IgG), to form an antigen-antibody complex. The vinyl-rabbit IgG is then co-polymerized with acrylamide (AAm) as a comonomer an N,N methylenebisacrylamide (MBAA) as a cross-linker in the presence of GAR IgG, resulting in responsive matrix 402 containing antigen-antibody bond sites 405, 406. One or more device 400 is mixed into a buffer solution with rabbit IgG. In the presence of free rabbit IgG, the antigen-antibody entrapment hydrogel matrix 402 will swell in proportion to the concentration of free rabbit IgG. Free IgG induces disassociation of antigen-antibody bonds grafted to inside responsive polymer matrix 402, due to the stronger affinity of antibody for the free antigen than the for antigen grafted to the network of polymer within responsive matrix 402. Therefore, responsive polymer matrix 402 swells in the presence of the free antigen because of disassociation of antigen-antibody bonds resulting in a decreased in cross linking density. Swelling due to the presence of free antigen increases the specific volume fraction of polymer matrix 402 resulting in an increase of the NMR relaxation rates (e.g., 1/T1, 1/T2). The NMR echo signals may be used to detect amount or concentration of free antigen. For example, free antigen concentration is inversely proportional to NMR relaxation rate (e.g., 1/T2).

In an illustrative, constructive embodiment, device 500 of FIG. 5 is designed as a glucose nanosensor. Responsive matrix 502 comprises poly (2-glucosyloxyethel methacrylate) (PGEMA) with binding moieties 505, pendant glucose groups, having affinity for binding moiety 506 which is Con A. Device 500 in an aqueous solution is flocculated by the addition of Con A through the complex formation between Con A and the pendant glucose groups of PGEMA. In the he presence of free glucose hydrogel matrix 502 will swell in proportion to the concentration of free glucose. Free glucose induces disassociation of the complex formation between Con A and pendant glucose groups of PGEMA inside responsive polymer matrix 502, due to the stronger affinity of the Con A for free glucose than pendant glucose groups of PGEMA grafted to the network of polymer within responsive matrix 502. Therefore, responsive polymer matrix 502 swells in the presence of the free glucose because of disassociation of the complexation bonds between Con A and pendant glucose groups of PGEMA resulting in a decreased in cross-linking density. Swelling due to the presence of free glucose increases the specific volume fraction of responsive 502, resulting in an increase of NMR relaxation rates (e.g., 1/T1, 1/T2). NMR echo signals may be used to detect amount or concentration of free glucose. For example, free glucose concentration is inversely proportional to NMR relaxation rate (e.g., 1/T2).

In FIG. 10 and FIG. 11, a principle on which the invention is based is explained on the basis of one embodiment, and serves not to limit the invention to a particular embodiment but for the purpose of explaining the principle. FIG. 10A shows the theoretical shift in T2 obtained by increasing size of a nanosensor. As particle diameter increases, T2 decreases in response to a certain point of diminishing return, where the T2 measurement begins to flatten out then reverses and increases with further increases in particle size. Provided methods comprise addition of a binding agent to a single population of analyte-bound nanoparticles. The method involves coating a nanoparticle with a single layer of analyte, and a single layer of binding agent. Addition of binding agent in this assay format leads to a uniform increase in size among all nanoparticles. Sze increase is dependent on concentration of binding agent and size of the binding agent and analyte, which are each highly adjustable. We hypothesize that this layer formation is thermodynamically and sterically favorable over cluster formation. Further, provided methods result in formation (or dispersion) and assay of a single population of non-aggregated nanosensors, thereby allowing for optimized and accurate measurements of relaxation parameters.

Provided methods comprise competitive assays which take advantage of these benefits. Methods comprise competitive assays consisting of inhibitive competitive assays, wherein formation of nanosensor coating is competitive, as well as dispersive competitive assays, wherein dispersion of pre-formed nanosensor coating is competitive. FIG. 11A depicts a schematic of one preferred format for a competitive coating assay according to the provided methods. Analyte, optional analyte analog, and binding agent (depicted in the scheme as antibody) are selected depending on the analyte desired for detection. Further, the type, size, or modification of binding agent is selected to optimize particle size when a nanosensor is saturated, for optimal relaxation measurements, and detection of analyte. Exemplary reagent production and uses in detection assays are provided below.

Crosslinked Iron Oxide Particle Synthesis

Nanoparticles were prepared according to methods known in the art. Briefly, T-10 dextran was dissolved in water mixed with ferric chloride and degassed by nitrogen purging. Ferric chloride solution was added to the mixture and the pH brought to 10 with ammonium hydroxide. Resulting monodisperse iron oxide (MION) particles were crosslinked with epichlorohydrin and ammonia to provide stability and amine groups for conjugation to targeting moieties to produce crosslinked iron oxide (CLIO) nanoparticles. Fluorescein decorated CLIOs were prepared by incubating aminated 30 nm CLIO nanoparticles with fluorescein isothiocynate (FITC). Unreacted FITC was then removed by size exclusion gel filtration in columns packed with Sephadex G-25 beads. Conjugated FITC-CLIO nanoparticles were characterized with an iron assay for particle concentration as well as against a fluorescent standard curve to measure the number of fluorescein molecules per particle.

Optimization of Particle Size and Relaxation Measurement

Anti-fluorescein antibody coating assays were performed by titrating in varying amounts of antibody (either anti-FITC antibody or anti-FITC antibody conjugated to an 80 kDa alkaline phosphatase (AP) protein) in to a fixed concentration of nanoparticles. Fluorescein decorated CLIO nanoparticles prepared as described above were incubated with binding agent (antibody/conjugated antibody) for a desired length of time at 37° C. and then $T_2$ relaxation times were measured on a Bruker Minispec. The coating assay had several unique advantages over nanoparticle clustering assays. The coating assay format was energetically favorable for the specific nanoparticle/antibody combinations tested which allowed the measured T2 switch to be robust and controllable. The recovery of the switch in a competitive assay is therefore also straightforward. As discussed above, and depicted in FIG. 10A, a decrease in measured T2 relaxation time is enhanced when a binding agent size is increased (e.g., antibody tethered to a large molecule (e.g., a protein, antibody, conjugated antibody)), which effectively results in a thicker coat around a nanoparticle. FIG. 10B shows the experimental results of coating assays using anti-flourescein antibody or antibody conjugated to alkaline phosphatase. As more antibodies are titrated in to the reaction and more nanoparticles become saturated with antibody, the T2 decreases in response. The curve shape was steeper with the anti-FITC-AP titration indicating that the particles are coated with a larger coating thickness as compared to the anti-FITC antibody case. Particle size measurements (using a Malvern Zetasizer) of nanosensors with increasing amounts of antibody or AP-conjugated antibody confirm the size increases with increasing antibody as well as further increases using conjugated antibody, and corroborate the hypothesis that the particles are being coated with anti-FITC-antibodies and with anti-FITC-AP antibodies. As antibody concentration was increased, the measured size of the nanoparticle increases proportionately. The T2 graph and size measurements also demonstrated a limitation of the coating assay format. Further increasing the size of the coating with binding agent will enhance the T2 switch with diminishing returns until the T2 flattens out and then begins to increase with size as shown FIG. 10A. Once a particle is fully coated with antibody, further changes in T2 cannot be measured unless the coating is disrupted.

Competitive Assays

Prepared nanoparticles were used in two different fluorescein competitive assay formats—inhibitive and competitive (dispersive) Inhibitive assays were performed by pre-incubating varying concentrations of fluorescein analyte with a fixed amount of anti-fluorescein antibody prior to incubation with prepared nanoparticle. For the competitive (dispersive) format, fluorescent analyte was incubated with a prior prepared antibody-nanoparticle solution. Both competitive formats demonstrated a positive correlation between measured T2 and analyte concentration as shown in FIG. 11A.

Inhibitive assays were performed in two-steps by pre-incubating varying concentrations of fluorescein analyte with a fixed amount of anti-fluorescein antibody prior to incubation with nanoparticle. For example, 80 ul of 62.5 ug/ml anti-FITC-AP antibody was fixed with a varying concentration of fluorescein sodium salt (analyte). The solution was incubated for 30 min at 37°. After pre-incubation, 240 ul of 0.067 mM [Fe] nanoparticles prepared as described above were added. The complete solution was incubated for 15 min at 37° followed by measurement of $T_2$ relaxation times on a Bruker Minispec. Results are shown in FIG. 12A.

The competitive (dispersive) format involved incubating fluorescent analyte in one step with a pre-incubated antibody-nanoparticle solution. For this assay, 3 concentrations of anti-FITC-AP antibody (125, 250 or 500 ul/ml) were mixed with a fixed concentration of nanoparticles. The solution was incubated at 37° prior to adding varying concentrations of fluorescein (analyte). The complete solution was incubated at 37° followed by measurement of $T_2$ relaxation times on a Bruker Minispec. Results are shown in FIG. 12B.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for detection of an analyte in a sample, the method comprising:
    (a) providing nanosensors, wherein the nanosensors comprise magnetic nanoparticles linked to a responsive polymer matrix and one or more binding moieties linked thereto, the binding moieties responsive to said analyte or analog thereof;
    (b) providing a fluid sample comprising an analyte or an analog thereof and placing the sample and the nanosensors in a container under conditions and for a sufficient period of time to allow the analyte to bind to and compete off the binding moiety from the nanosensor, thereby changing the specific volume of the responsive polymer matrix, leading to a change in one or more relaxivity parameters of the sample in the container;
    (c) placing the container in proximity to an NMR detector;
    (d) measuring the change in the one or more relaxivity parameters of the sample in the container; and
    (e) determining one or more attributes relative to the sample;
    wherein the nanoparticle, binding moiety and analyte or analog thereof linked to the nanoparticle are size optimized to confer optimal relaxation measurements.

2. The method of claim 1, wherein the attribute is selected from the group consisting of presence of the analyte, amount of the analyte, and concentration of the analyte.

3. The method of claim 1, wherein the analyte comprises at least one member selected from the group consisting of a protein, a peptide, a polypeptide, an amino acid, a nucleic acid, an oligonucleotide, a therapeutic agent, a metabolite of a therapeutic agent, RNA, DNA, an antibody, an organism, a virus, a bacteria, a carbohydrate, and a polysaccharide.

4. The method of claim 1, wherein the binding moiety comprises an antibody or a conjugated antibody.

5. The method of claim 4, wherein the antibody is a monoclonal antibody.

6. The method of claim 1, wherein the fluid sample is water, saline, buffered saline, or a biological fluid.

7. The method of claim 6, wherein the biological fluid is blood, a cell homogenate, a tissue homogenate, a cell extract, a tissue extract, a cell suspension, a tissue suspension, milk, urine, saliva, semen, or spinal fluid.

* * * * *